United States Patent
Bogusky et al.

(10) Patent No.: US 12,004,710 B2
(45) Date of Patent: Jun. 11, 2024

(54) SYSTEMS AND METHODS FOR HOLDING A FLEXIBLE ELONGATE DEVICE IN A POSE

(71) Applicant: INTUITIVE SURGICAL OPERATIONS, INC., Sunnyvale, CA (US)

(72) Inventors: Joseph D. Bogusky, San Jose, CA (US); Randall L. Schlesinger, San Mateo, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 707 days.

(21) Appl. No.: 17/254,122

(22) PCT Filed: Jun. 19, 2019

(86) PCT No.: PCT/US2019/037954
§ 371 (c)(1),
(2) Date: Dec. 18, 2020

(87) PCT Pub. No.: WO2019/246240
PCT Pub. Date: Dec. 26, 2019

(65) Prior Publication Data
US 2021/0268233 A1    Sep. 2, 2021

Related U.S. Application Data

(60) Provisional application No. 62/687,120, filed on Jun. 19, 2018.

(51) Int. Cl.
*A61M 25/01*    (2006.01)
*A61B 1/00*    (2006.01)
(Continued)

(52) U.S. Cl.
CPC ...... *A61B 1/00078* (2013.01); *A61B 1/00147* (2013.01); *A61B 1/009* (2022.02);
(Continued)

(58) Field of Classification Search
CPC . A61B 1/00078; A61B 1/00147; A61B 1/009; A61B 2034/2051;
(Continued)

(56) References Cited

U.S. PATENT DOCUMENTS 5,251,611 A    10/1993    Zehel et al.
5,759,151 A    6/1998    Sturges
(Continued)

FOREIGN PATENT DOCUMENTS

CN    107921236 A    4/2018
WO    WO-2013056006 A2    4/2013
(Continued)

OTHER PUBLICATIONS

International Preliminary Report on Patentability for Application No. PCT/US2019/037954, dated Dec. 30, 2020, 08 pages.
(Continued)

*Primary Examiner* — Julian W Woo
(74) *Attorney, Agent, or Firm* — Haynes & Boone, LLP.

(57) ABSTRACT

Stiffening mechanisms or systems that assist or enable holding a pose or shape of a flexible body may be part of a steering mechanism for an end effector. The stiffening mechanisms may be separately actuated and/or may themselves also enable steering of a flexible elongate device. Further, the stiffening mechanisms may use information from sensor systems, such as a shape sensor in the form of an optical fiber, a plurality of EM sensors distributed along the length of a flexible device, and/or navigation systems, such as a sensor system that computes the approximate location of medical instruments (such as a flexible body)

(Continued)

within the anatomy of the patient and/or medical tools that are delivered through a main lumen of the flexible body, to inform a control system which then controls formation and holding of a shape of the flexible body.

21 Claims, 11 Drawing Sheets

(51) Int. Cl.
*A61B 1/005* (2006.01)
*A61B 34/20* (2016.01)
*A61B 34/35* (2016.01)

(52) U.S. Cl.
CPC .... *A61M 25/0138* (2013.01); *A61M 25/0147* (2013.01); *A61M 25/0155* (2013.01); *A61B 2034/2051* (2016.02); *A61B 2034/2061* (2016.02); *A61B 34/35* (2016.02); *A61M 2205/0266* (2013.01)

(58) Field of Classification Search
CPC . A61B 2034/2061; A61B 2017/00318; A61M 25/0138; A61M 25/0147; A61M 25/0155; A61M 2205/0266
See application file for complete search history.

(56) References Cited

U.S. PATENT DOCUMENTS

| 6,380,732 | B1 | 4/2002 | Gilboa |
| 6,389,187 | B1 | 5/2002 | Greenaway et al. |
| 6,610,007 | B2 | 8/2003 | Belson et al. |
| 6,974,411 | B2 | 12/2005 | Belson |
| 7,316,681 | B2 | 1/2008 | Madhani et al. |
| 7,772,541 | B2 | 8/2010 | Froggatt et al. |
| 8,900,131 | B2 | 12/2014 | Chopra et al. |
| 9,138,166 | B2 * | 9/2015 | Wong ............ A61B 5/065 |
| 9,259,274 | B2 | 2/2016 | Prisco |
| 9,452,276 | B2 | 9/2016 | Duindam et al. |
| 10,737,073 | B2 * | 8/2020 | Barrish ............ A61M 25/1025 |
| 11,678,788 | B2 | 6/2023 | Bogusky et al. |
| 2006/0013523 | A1 | 1/2006 | Childers et al. |
| 2013/0096385 | A1 | 4/2013 | Fenech et al. |
| 2017/0021132 | A1 | 1/2017 | Laby et al. |
| 2018/0056040 | A1 | 3/2018 | French et al. |
| 2020/0030575 | A1 | 1/2020 | Bogusky et al. |

FOREIGN PATENT DOCUMENTS

| WO | WO-2015061692 A1 | 4/2015 |
| WO | WO-2016160586 A1 | 10/2016 |
| WO | WO-2016191298 A1 | 12/2016 |
| WO | WO-2017044874 A1 | 3/2017 |
| WO | WO-2017139591 A1 | 8/2017 |
| WO | WO-2017139621 A1 | 8/2017 |
| WO | WO-2018005928 A1 | 1/2018 |
| WO | WO-2018145100 A1 | 8/2018 |
| WO | WO-2019246240 A1 | 12/2019 |

OTHER PUBLICATIONS

International Search Report and Written Opinion for Application No. PCT/US2019/037954, dated Sep. 30, 2019, 13 pages (ISRG12990/PCT).

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

\* cited by examiner

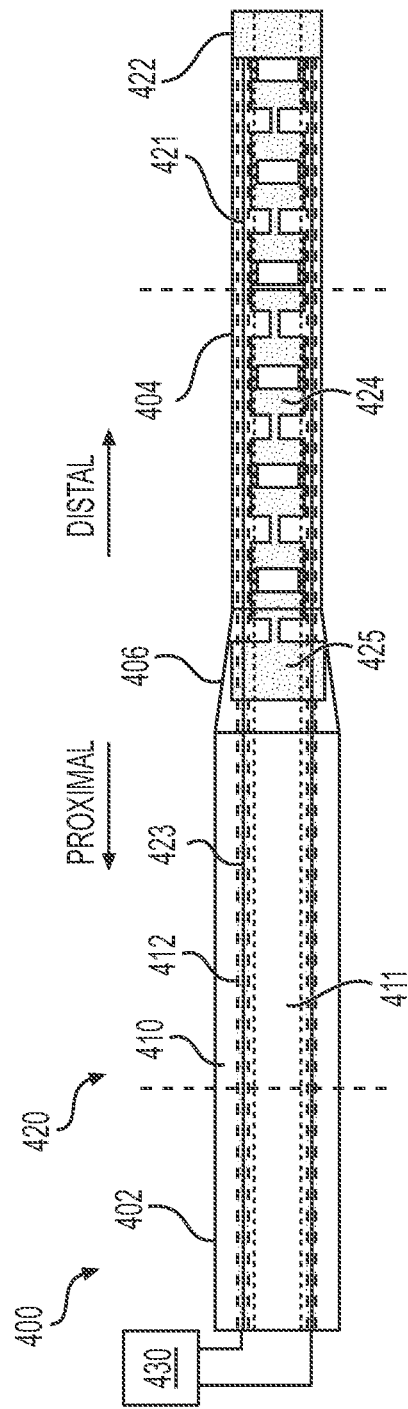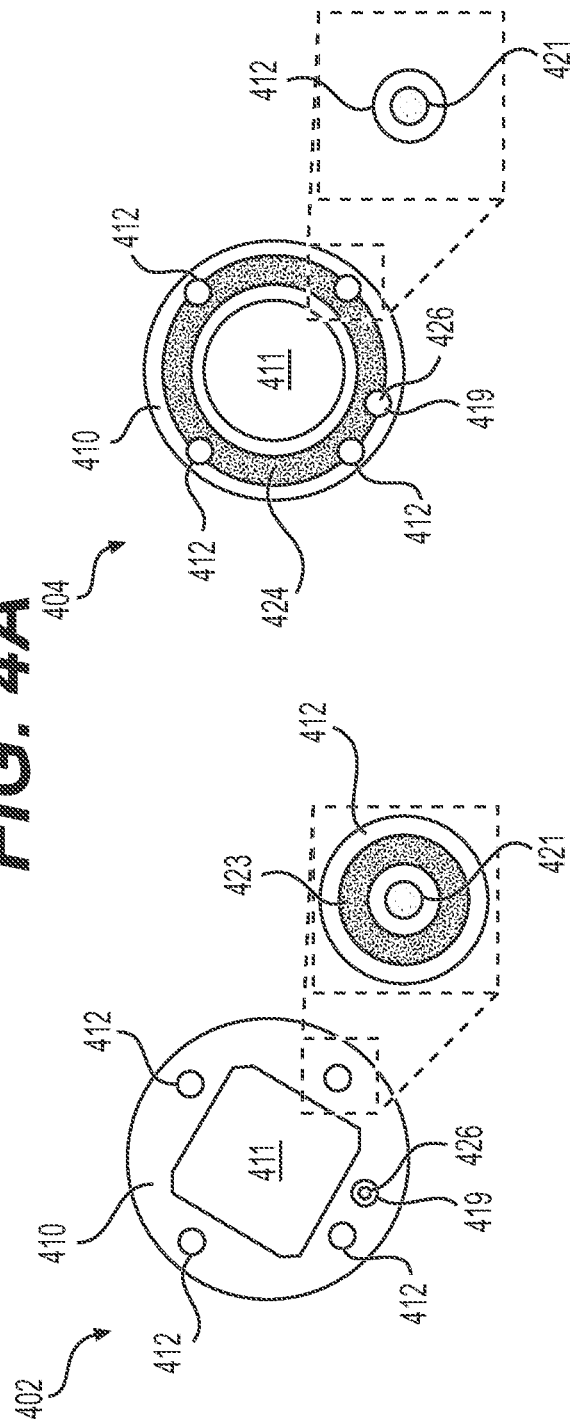

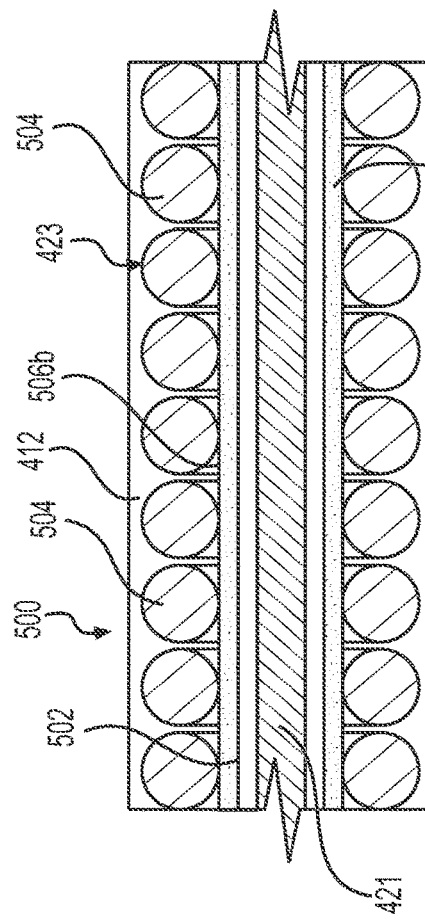
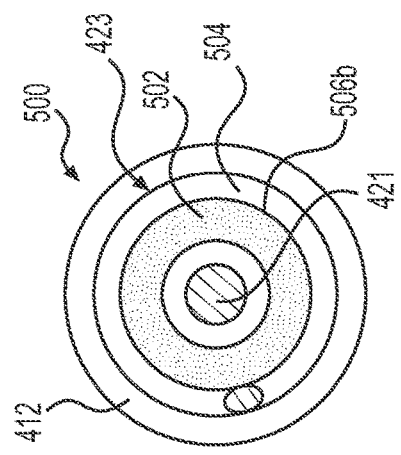
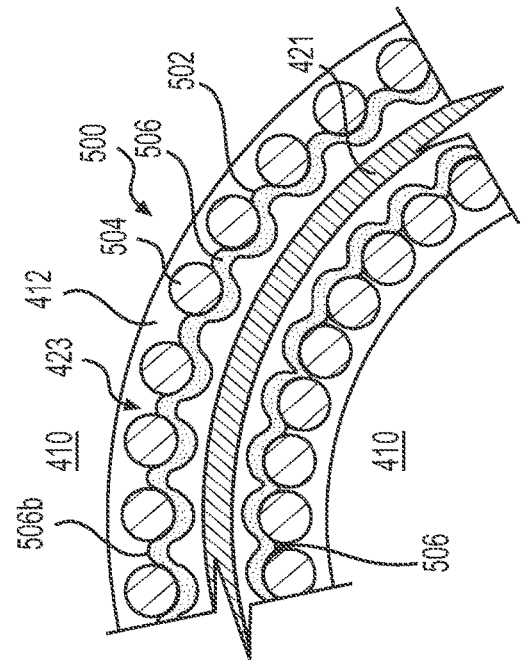
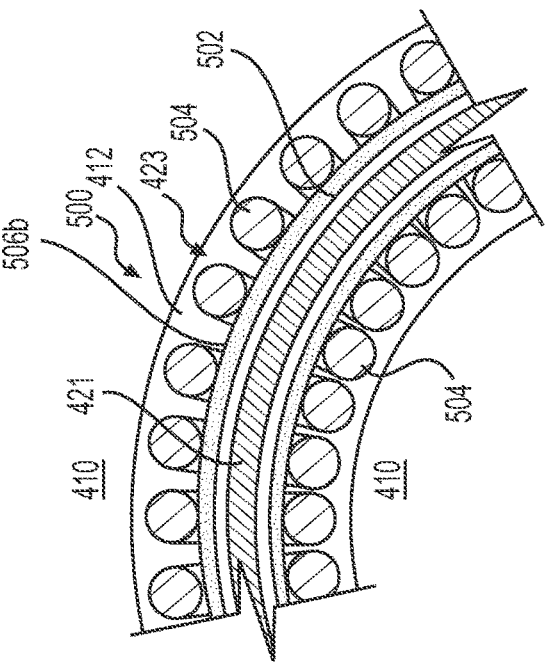
FIG. 7B
FIG. 7D
FIG. 7A
FIG. 7C

SYSTEMS AND METHODS FOR HOLDING A FLEXIBLE ELONGATE DEVICE IN A POSE

CROSS REFERENCE TO RELATED APPLICATIONS

This application is a national stage application filed under 35 U.S.C. § 371 of PCT/US2019/037954 filed Jun. 19, 2019, which claims the benefit of U.S. Provisional Patent Application Ser. No. 62/687,120 filed Jun. 19, 2018, the disclosures of which are expressly incorporated herein by reference.

TECHNICAL FIELD

The present disclosure is directed to teleoperated systems and in particular teleoperated systems involving use of flexible elongate devices.

BACKGROUND

Flexible elongate devices can be employed in range of fields needing access to restricted openings such as for the exploration of pipes or in medical procedures, especially minimally invasive medical techniques.

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions physician may insert minimally invasive medical instruments (including surgical, diagnostic, therapeutic, or biopsy instruments) to reach a target tissue location.

One such minimally invasive technique is to use a flexible and/or steerable elongate device, such as a flexible catheter, that can be inserted into anatomic passageways and navigated toward a region of interest within the patient anatomy. In some applications, the flexible and/or steerable elongate device needs to be held in a particular shape to enable or improve the safety of a procedure. It would be advantageous to provide improvements to systems and methods for holding a flexible elongate device in a desired pose.

SUMMARY OF THE INVENTION

Disclosed herein are a range of stiffening mechanisms or systems that assist or enable holding a pose or shape of a flexible body. These stiffening mechanisms may be part of the steering mechanism, may be separately actuated and/or may themselves also enable steering of the flexible elongate device. Further, the stiffening mechanisms may use information from sensor systems, such as a shape sensor in the form of an optical fiber, a plurality of EM sensors distributed along the length of a flexible device, and/or navigation systems, such as a sensor system that computes the approximate location of medical instruments (such as a flexible body) within the anatomy of the patient and/or medical tools that are delivered through a main lumen of the flexible body, to inform a control system which then controls formation and holding of a shape of the flexible body.

One embodiment includes a flexible elongate device having a flexible body, a support structure, and a stiffening mechanism. The flexible body has a proximal end, a distal end, and at least one lumen extending between the proximal and distal ends. The flexible body has sufficient flexibility to form a pose. The support structure is coupled with the flexible body. The support structure includes a plurality of sub-elements arranged in series. At least a portion of the sub elements are configured to spread apart when the flexible body flexes into the pose. The stiffening mechanism has at least one stiffening element extending along at least a portion of the flexible body and is configured for actuation independent of the support structure. Actuation of the at least one stiffening element stiffens the support structure to hold at least a portion of the pose of the flexible body. The stiffening element includes a compression feature configured to engage the support structure.

The support structure includes a coil and the sub-elements include windings of the coil in another embodiment. The support structure includes a spine in another embodiment.

In various embodiments, the stiffening mechanism includes an inflatable system wherein the inflatable system includes a balloon configured to engage the support structure. The balloon can be configured to extend in between the sub-elements. For example, the balloon can be configured to extend between the sub-elements due to application of a vacuum pressure causing the balloon to collapse into an exterior of the support structure and in between the sub-elements. In yet another embodiment, the balloon is configured to extend in between the sub-elements due to the application of an inflation pressure causing the balloon to expand into an interior defined within the support structure and in between the sub-elements.

The balloon system, in other embodiments, includes a plurality of balloon portions. For example, the balloon portions can be selectively inflatable to hold the at least the portion of the pose. The balloon portions can be positioned between the sub elements. Further, the balloon portions can spiral between the sub elements.

In yet another embodiment, the stiffening mechanism can comprise a plurality of control elements extending along the flexible body and configured to exert tension on the flexible body in conjunction with selective inflation of the balloon portions to further hold the at least the portion of the pose.

Other embodiments can include a shape sensor configured to determine the pose of the flexible body and a controller. The controller can be connected in communication with the shape sensor and the controller is configured to activate the stiffening mechanism to hold at least the portion of the pose of the flexible body.

In another embodiment, the medical system includes a flexible body, a shape sensor, a stiffening mechanism and a controller. The flexible body has a proximal end, a distal end, and at least one lumen extending between the proximal and distal ends, wherein the flexible body includes a plurality of sub-portions. The shape sensor extends along at least a portion of the flexible body. The stiffening mechanism has a plurality of stiffening elements, each of the stiffening elements positioned within one of the plurality of sub-portions, wherein the sub-portions extend along the flexible body. The controller is connected in communication with the shape sensor, configured to selectively activate the stiffening elements based in part on data received from the shape sensor.

In another embodiment, the controller is further configured to selectively activate the stiffening elements based in part on a type of instrument for insertion through the flexible body. For example, the controller can be configured to energize selected ones of the stiffening elements to reduce curvature of the flexible body to match a stiff type of instrument.

In another embodiment, the controller is further configured to selectively activate the stiffening elements based in part on anatomical information. The anatomical information can also information identifying a target area of anatomy and wherein the controller is further configured to actuate selected ones of the stiffening elements to protect the target area of anatomy.

In another embodiment, the shape sensor includes at least one of a shape sensing fiber extending along the flexible body or a plurality of EM sensors extending along the flexible body.

In other embodiments, the stiffening mechanism includes a longitudinal balloon array having a plurality of balloon portions and wherein each of the stiffening elements is one of the plurality of balloon portions.

In another embodiment, the flexible body includes a coil with a plurality of adjacent windings and wherein each of the balloon portions are configured to extend between the adjacent windings with the application of pressure. Further, controller may be configured to selectively apply pressure to each of the balloon portions to urge apart adjacent windings to shape the flexible body.

Other embodiments further comprise a steering mechanism configured to control the distal end portion of the flexible body. For example, the steering mechanism can include a plurality of pull wires and wherein the controller is further configured to adjust tension in the pull wires along with selective activation of the stiffening elements to hold the portion of the flexible body in the pose.

In other embodiments, the plurality of stiffening elements includes a plurality of nitinol actuators. For example, the flexible body can include a wall structure and the plurality of nitinol actuators are embedded in the wall structure. The plurality of nitinol actuators can be distributed circumferentially within the wall structure.

Other embodiments include a method of holding at least a portion of a pose of a flexible body. The method can include engaging a stiffening element of a stiffening mechanism within a spacing between at least a pair of the plurality of sub-elements, wherein the plurality of sub-elements extend along the flexible body.

In another embodiment, engaging stiffening element includes urging a portion of the stiffening element into the spacing between the at least the pair of the plurality of sub-elements.

In another embodiment, urging the portion of the stiffening element includes one of inflating or deflating the stiffening element.

In another embodiment, actuating a plurality of pull wires extending within a wall structure of the flexible body including adjusting tension in the plurality of pull wires while selectively activating the stiffening elements to hold the pose of the flexible body.

Other embodiments include a method of holding a pose of a flexible body using a controller. The method includes measuring a current configuration of a flexible body based at least in part on a sensor coupled to the flexible body, determining a desired configuration of the flexible body, and selectively activating a stiffening mechanism to position the flexible body from the current configuration to the desired configuration, wherein the stiffening mechanism includes a plurality of stiffening elements distributed down the length of the flexible body.

In another embodiment, positioning the flexible body in the desired configuration includes activating each of the plurality of stiffening elements independently.

In another embodiment, the current configuration includes a measured shape of the flexible body.

In another embodiment, the method can comprise identifying a small radius in the measured shape, wherein selectively activating the stiffening mechanism includes activating select ones of the plurality of the stiffening elements to increase a bend radius of the flexible body at the identified small radius in the measured shape.

In another embodiment, the method can comprise receiving information describing stiffness of an instrument to be delivered by the flexible body, wherein the identifying of the small radius in the measured shape includes determining a minimum bend radius corresponding to the stiffness of the instrument.

In another embodiment, determining the desired configuration comprises receiving information identifying a target area of anatomy and setting the desired configuration to activate select ones of the plurality of the stiffening elements at the identified target area of anatomy. The information received identifying the target area of anatomy may be based on live imaging.

In another embodiment, determining the desired configuration comprises receiving a preoperatively recorded surgical image, registering the flexible body to the preoperatively recorded surgical image using sensor data from the sensor coupled to the flexible body, and identifying a portion of the flexible body positioned within the identified target area of anatomy based on the registration. The information received identifying the target area of anatomy is based on the preoperatively recorded surgical image In other embodiments, the plurality of the stiffening elements includes a plurality of nitinol actuators extending within a wall structure of the flexible body, and wherein the selectively activating the stiffening mechanism includes energizing at least one of the plurality of nitinol actuators.

In yet other embodiments, the plurality of the stiffening elements includes a plurality of balloons, and wherein the selectively activating the stiffening mechanisms includes inflating or deflating at least one of the plurality of balloons.

Embodiments of the present invention have a range of advantages. For example, in the environment of articulating devices that navigate the tortuosity of human anatomy, it is advantageous to securely hold the contorted position of said device while instruments are being delivered through the device. Frequently, devices that pass through an articulating device will exert forces that have a tendency to straighten a contorted and articulated portion of the device. Embodiments of the invention provides various apparatus and methods to hold the pose of a catheter in a contorted position for stable delivery of instruments

BRIEF DESCRIPTIONS OF THE DRAWINGS

FIGS. 4A-4C are simplified diagrams of a flexible elongate device according to some embodiments.

FIGS. 7A-7D are simplified diagrams of a stiffening mechanism or system according to some embodiments.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
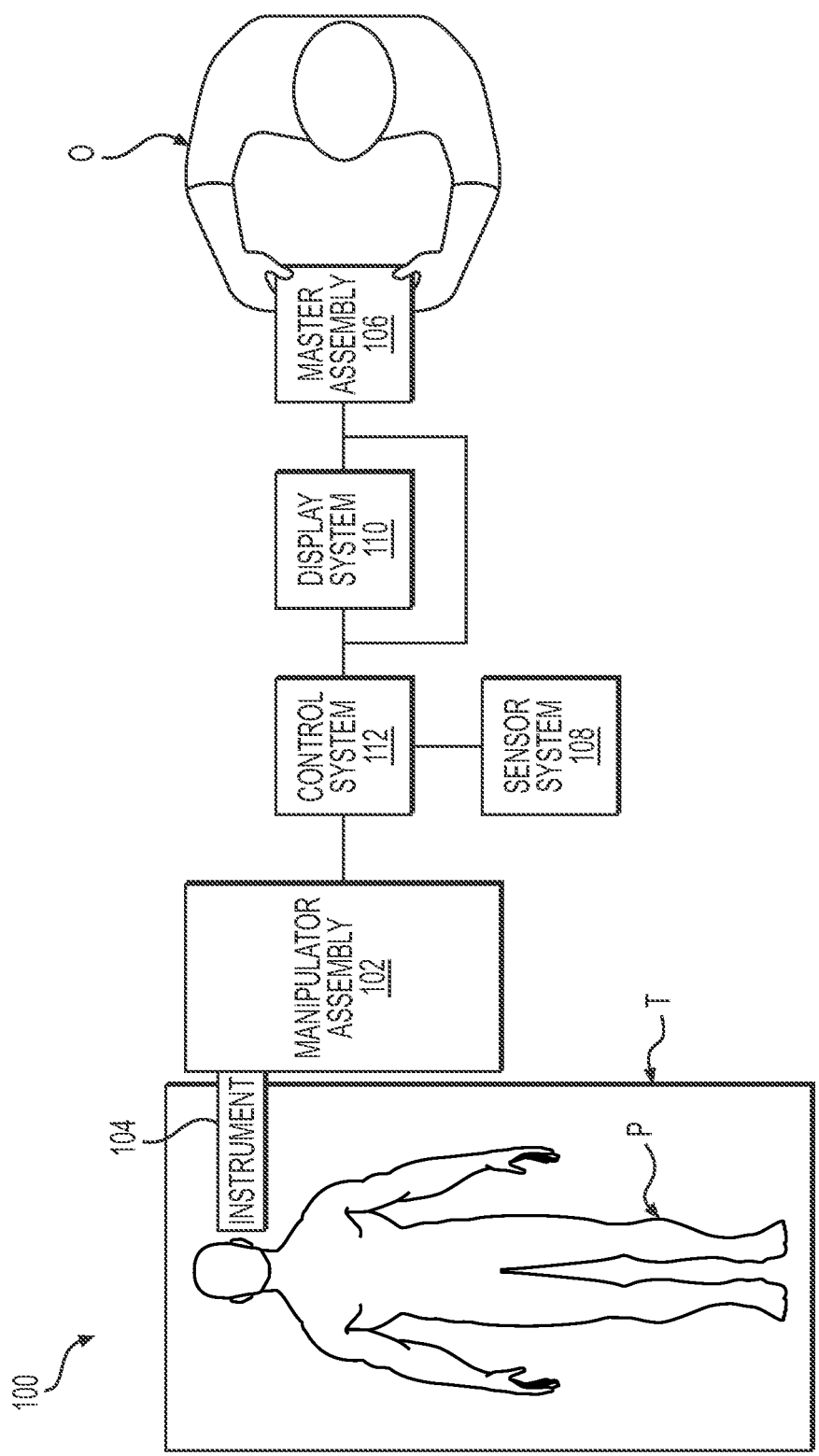
FIG. 1 is a simplified diagram of a teleoperated medical system according to some embodiments.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems and general robotic or teleoperational systems.

As shown in FIG. 1, medical system 100 generally includes a manipulator assembly 102 for operating a medical instrument 104 in performing various procedures on a patient P. The manipulator assembly 102 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. Manipulator assembly 102 is mounted to or near an operating table T. A master assembly 106 allows an operator (e.g., a surgeon, a clinician, or a physician as illustrated in FIG. 1) to view the interventional site and to control manipulator assembly 102. Master assembly 106 generally includes one or more control devices for controlling manipulator assembly 102.

Manipulator assembly 102 supports medical instrument 104 and may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Teleoperated medical system 100 also includes a display system 110 for displaying an image or representation of the surgical site and medical instrument 104 generated by sub-systems of sensor system 108. Display system 110 and master assembly 106 may be oriented so operator O can control medical instrument 104 and master assembly 106 with the perception of telepresence. Display system 110 may present images of a surgical site recorded pre-operatively or intra-operatively using image data from imaging technology such as, computed tomography (CT), magnetic resonance imaging (MM), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity-based information) images and/or as images from models created from the pre-operative or intra-operative image data sets. In some embodiments, often for purposes of imaged guided surgical procedures, display system 110 may display a virtual navigational image in which the actual location of medical instrument 104 is registered (i.e., dynamically referenced) with the preoperative or concurrent images/model.

In some embodiments, display system 110 may display a virtual navigational image in which the actual location of medical instrument 104 is registered with preoperative or concurrent images to present the operator O with a virtual image of medical instrument 104 within the surgical site from an external viewpoint. An image of a portion of medical instrument 104 or other graphical or alphanumeric indicators may be superimposed on the virtual image to assist operator O in the control of medical instrument 104. As described herein, visual representations of data points may be rendered to display system 110. For example, measured data points, moved data points, registered data points, and other data points described herein may be displayed on display system 110 in a visual representation.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of manipulator assembly 102 to move medical instrument 104. Control system 112 may optionally further include a virtual visualization system to provide navigation assistance to operator O when controlling medical instrument 104 during an image-guided surgical procedure.

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system. For example, PCT Publication WO 2016/191298 (published Dec. 1, 2016) (disclosing "Systems and Methods of Registration for Image Guided Surgery"), which is incorporated by reference herein in its entirety, discloses such one system.

Figure 2A:
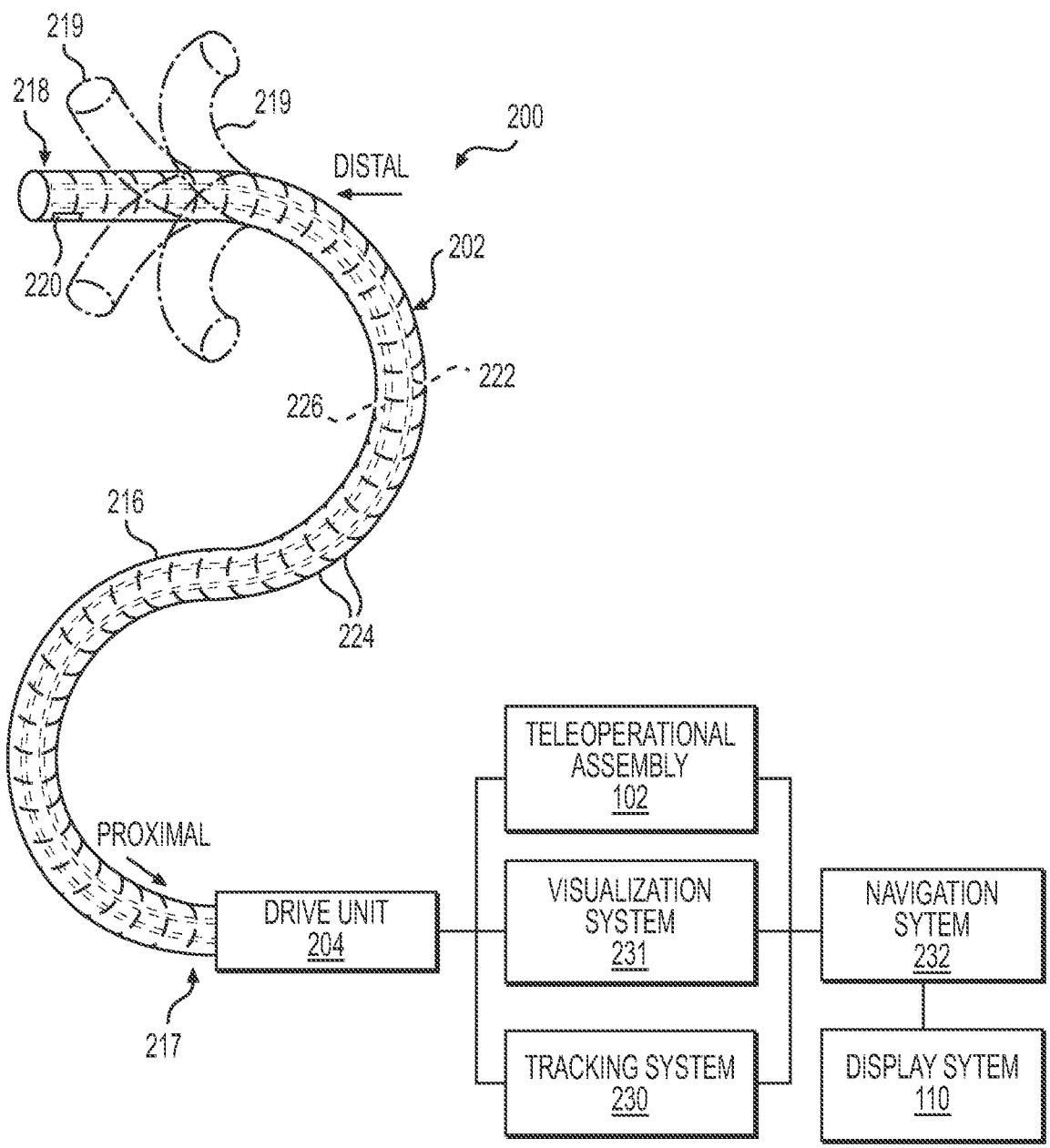
FIG. 2A is a simplified diagram of a medical instrument system according to some embodiments.

FIG. 2A is a simplified diagram of a medical instrument system 200 according to some embodiments. Medical instrument system 200 includes elongate device 202, such as a flexible catheter, coupled to a drive unit 204. Elongate device 202 includes a flexible body 216 having proximal end 217 and distal end or tip portion 218.

Medical instrument system 200 further includes a tracking system 230 for determining the position, orientation, speed, velocity, pose, and/or shape of distal end 218 and/or of one or more segments 224 along flexible body 216 using one or more sensors and/or imaging devices as described in further detail below. The entire length of flexible body 216, between distal end 218 and proximal end 217, may be effectively divided into segments 224. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 µm. In other embodiments, the dimensions may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties.

In some embodiments, tracking system 230 may optionally and/or additionally track distal end 218 using a position sensor system 220. Position sensor system 220 may be a component of an EM sensor system with position sensor system 220 including one or more conductive coils that may be subjected to an externally generated electromagnetic field. Each coil of the EM sensor system then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety. In some examples, a series of positional sensors (not shown), such as electromagnetic (EM) sensors similar to the sensors in position sensor 220 may be positioned along flexible body 216 and then used for shape sensing. Flexible body 216 includes a channel 221 sized and shaped to receive a medical instrument 226.

Figure 2B:
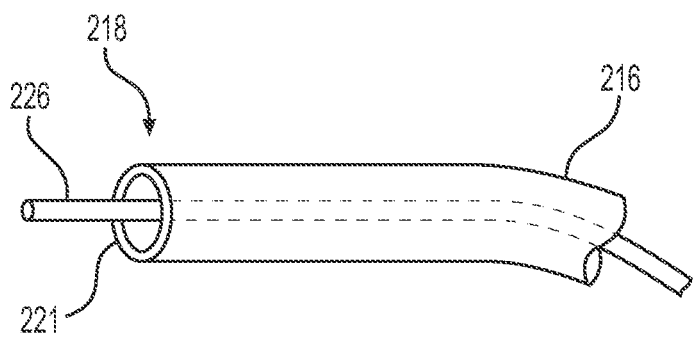
FIG. 2B is a simplified diagram of a medical instrument with an extended medical tool according to some embodiments.

FIG. 2B is a simplified diagram of flexible body 216 with medical instrument 226 extended according to some embodiments. In some embodiments, medical instrument 226 may be used for procedures such as surgery, biopsy, ablation, illumination, irrigation, or suction.

Medical instrument 226 may additionally house cables, linkages, or other actuation controls (not shown) that extend between its proximal and distal ends to controllably bend the distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. Steerable elongate devices are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

The information from tracking system 230 may be sent to a navigation system 232 where it is combined with information from visualization system 231 and/or the preoperatively obtained models (e.g., anatomic models of the patient anatomy) to provide the physician or other operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, manipulator assembly 102 of FIG. 1 may be replaced by direct operator control. In some examples, the direct operator control may include various handles and operator interfaces for hand-held operation of the instrument.

Figure 3A:
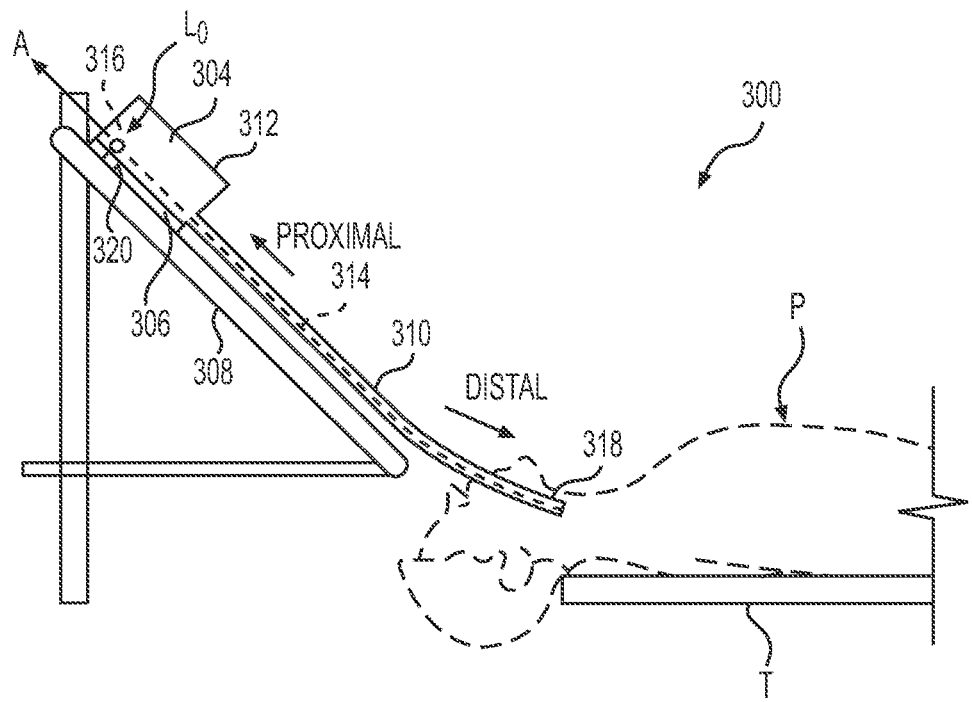
FIGS. 3A and 3B are simplified diagrams of side views of a patient coordinate space including a medical instrument mounted on an insertion assembly according to some embodiments.
Figure 3B:
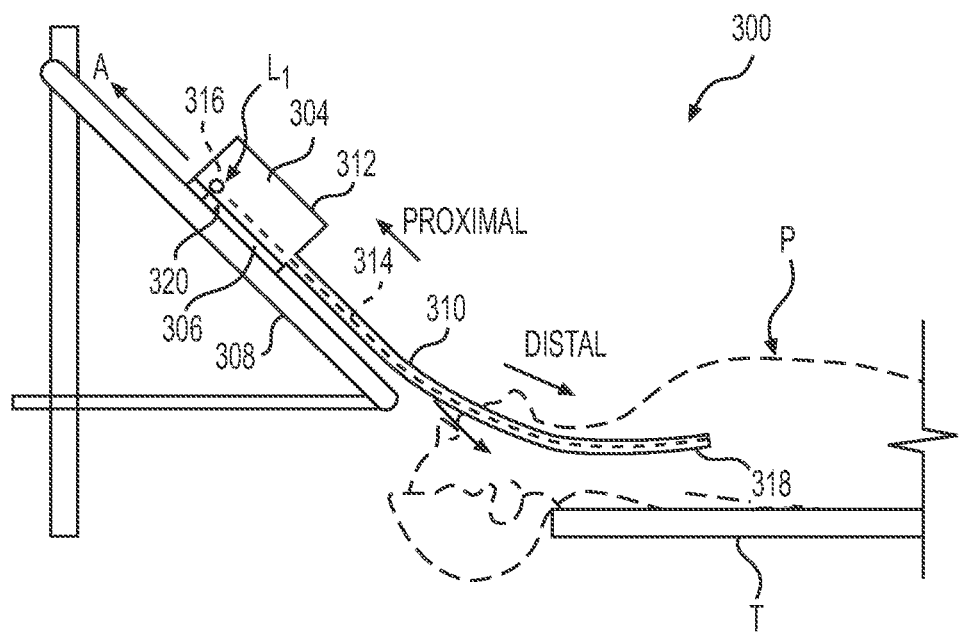

FIGS. 3A and 3B are simplified diagrams of side views of a patient coordinate space including a medical instrument mounted on an insertion assembly according to some embodiments. As shown in FIGS. 3A and 3B, a surgical environment 300 includes a patient P is positioned on the table T of FIG. 1. Instrument carriage 306 or insertion stage 308 may include actuators, such as servomotors, (not shown) that control motion of instrument carriage 306 along insertion stage 308. Elongate device 310 is coupled to an instrument body 312. Instrument body 312 is coupled and fixed relative to instrument carriage 306. In some embodiments, an optical fiber shape sensor 314 is fixed at a proximal point 316 on instrument body 312. Shape sensor 314 measures a shape from proximal point 316 to another point such as distal end 318 of elongate device 310. Point gathering instrument 304 may be substantially similar to medical instrument system 200. A position measuring device 320 provides information about the position of instrument body 312 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 3A shows instrument body 312 and instrument carriage 306 in a retracted position along insertion stage 308. In FIG. 3B, instrument body 312 and instrument carriage 306 have advanced along the linear track of insertion stage 308 and distal end 318 of elongate device 310 has advanced into patient P.

FIGS. 4A-4C are simplified diagrams of a flexible elongate device 400 according to some embodiments. According to some embodiments consistent with FIGS. 1-3, flexible elongate device 400 may correspond to elongate device 202 of medical instrument system 200. As depicted in FIG. 4A, flexible elongate device 400 can include a proximal section 402, a distal section 404 and a transition section 406 therebetween.

Flexible elongate device 400 can include a flexible body 410 with a flexible wall having a thickness extending from an inner surface to an outer surface of the flexible body 410. A main lumen 411 can extend within the flexible body 410, through the proximal section 402, the transition section 406, and the distal section 404. The main lumen 411 can provide a delivery channel for a medical tool, such as an endoscope, biopsy needle, ultrasound (EBUS or IVUS) probe, ablation tool, chemical delivery tool, and/or the like, to be inserted through flexible body 410. According to some embodiments, a plurality of control element lumens 412 extend through the flexible wall of the flexible body 410 arranged circumferentially in the flexible wall around the main lumen 411. According to some embodiments, a sensor lumen 419 extends through the flexible wall of the flexible body 410. The sensor lumen 419 can extend from the proximal end of the flexible elongate device 400, through the proximal section 402, transition section 406, terminating at a distal portion of the distal section 404. In some examples, flexible body 410 may include various other types of lumens for electrical wires, fibers, sensors, small medical instruments, chemical delivery, and/or the like. In alternative embodiments, flexible body 410 may include an all-purpose lumen that can be used for a variety of purposes, including accommodating multiple concurrently inserted instruments, control elements, sensors, and/or the like.

As depicted in FIGS. 4A-4C, within each of the control element lumens 412, a coil pipe or conduit 423 can extend through the proximal section 402 of the flexible body 410, providing channels through which a plurality of control elements 421 extends. In some examples, control elements 421 can include pull wires, tendons, push rods and/or the like. The conduits 423 terminate at the transition section 406, proximal to the distal section 404. The control elements 421 extend out of the conduits 423 at the transition section 406, entering the distal section 404 through control element lumens 412, and attach to a distal mount 422. The one or more control elements 421 can be used to actuate distal section 404 of flexible elongate device 400. As depicted in FIGS. 4B and 4C, four control elements 421 can be disposed within control element lumens 412 and evenly spaced around the circumference of flexible elongate device 400.

In the illustrative example provided in FIG. 4B, a pair of lumens that includes sensor lumen 419 and one of control element lumens 412 is approximately centered along a side of the rounded square formed by main lumen 411. Consequently, neither sensor lumen 419 nor control element lumens 412 are individually centered along the side of the rounded square. Moreover, because control elements 421 are equally spaced around the perimeter of the rounded square, none of the control element lumens 412 are centered relative to the rounded square. As a result, the square formed by control elements 421 and the rounded square formed by main lumen 411 are offset by approximately 30 degrees. However, it is to be understood that different numbers and/or arrangements of control elements 421 are possible. For example, control elements 421 may be unevenly spaced around the circumference of flexible elongate device 400 and/or centered relative to the sides of main lumen 411.

Distal section 404 is actuated by applying actuation forces to control elements 421 (e.g., pulling and/or pushing on control elements 421 in an unequal manner). Applying actuation forces causes distal section 404 to bend in the direction defined by the net actuation forces. In some examples, the actuation forces may be applied manually, robotically, and/or the like. For example, the actuation forces may be applied using an actuator 430 positioned at the proximal end of flexible elongate device 400. Conduits 423 transfer the actuation forces applied to control elements 421 from the proximal end to the distal end of proximal section 402 at transition section 406. Consequently, even when unequal actuation forces are applied to control elements 421, little actuation force appears within proximal section 402. In some examples, conduits 423 may be flexible to retain the flexibility of proximal section 402. Further examples of conduits are provided in P.C.T. Patent Application PCT/US14/62188 entitled "Flexible Instrument with Embedded Actuation Conduits," filed Oct. 24, 2014, which is hereby incorporated by reference in its entirety.

Any bend along the length of the proximal section 402 of the flexible elongate device 400 results in a change of length of control element lumens 412. For example, with reference to FIG. 4A, if the flexible body bends in a downward motion, the control element lumens 412 on the lower portion of flexible body 410 will decrease in length while the control element lumens 412 on the upper portion of flexible body will increase in length. Thus, it can be necessary for the conduits 423 to axially slide within the control element lumens 412. In some examples, the conduits can be constrained (e.g., fixed and/or prevented from sliding proximally along a conduit longitudinal axis) at a proximal end of the flexible elongate device within the actuator 430 and can terminate at the transition section 406. The conduits may be constrained (e.g., fixed and/or prevented from sliding distally along a conduit longitudinal axis) at the transition section 406. In this example, within transition section 406, a stopper 425 is coupled between conduits 423 on the stopper proximal side and an axial support structure 424 on the distal stopper side. Stopper 425 prevents conduits 423 from shifting distally along flexible elongate device 400. In alternative examples, the conduits may be fixed to stopper 425.

Within distal section 404, axial support structure 424 is configured to bend in response to actuation forces applied to control elements 421. Consequently, when unequal actuation forces are applied to control elements 421, distal section 404 bends in the direction defined by the net actuation forces. Axial support structure 424 supports distal section 404 against axial loads generated by the actuation forces applied to control elements 421. In particular, axial support structure 424 may prevent or reduce distortion, compression and/or collapse of distal section 404 under axial loads. Further examples of axial support structures are provided in U.S. Provisional Patent Application 62/378,943 entitled "Axial Support Structure for a Flexible Elongate Device," which is hereby incorporated by reference in its entirety.

Although axial support structure 424 is depicted as having a spine-like structure in FIG. 4A, other structures are possible. In some examples, axial support structure 424 may be formed as a single large coil that encloses main lumen 411. Additionally, while FIG. 4C illustrates control elements 421 within control element lumens 412, in a similar configuration as shown in FIG. 4B for proximal section 402, axial support structure 424 may be include conduits similar to conduits 423. In some embodiments, conduits 423 may continue to run through both proximal and distal sections of flexible body 420. In alternative embodiments, separate conduits 423 may run in the proximal section and distal section. Whereas the conduits of conduits 423 are arranged concentrically around control elements 421 to counteract the actuation forces applied to control elements 421, the conduits of axial support structure 424 may be offset from control elements 421 (e.g., located at different positions around the circumference of flexible body 410) to allow axial support structure 424 to bend in response to actuation forces. Alternately or additionally, the conduits of axial support structure 424 may be more flexible (e.g., smaller diameter and/or constructed using smaller gauge wire) than the conduits of conduits 423.

In some examples, one or more of lumens 411, 412, 419, and/or sections thereof, may be keyed. That is, a lumen and/or a portion of a lumen may have a non-circular cross-sectional shape that prevents or constrains the rotation of a tool (e.g., a medical instrument, sensor, fiber, electrical wire, actuation element, and/or the like) with a matching non-circular cross-sectional shape when inserted through the lumen. As depicted in FIG. 4B, main lumen 411 of proximal section 402 is keyed. In particular, the main lumen 411 has a rounded square cross-sectional shape that supports four keyed orientations.

In some examples, a localization sensor 426, such as an optical fiber of shape sensor 222, extends through sensor lumen 419. Like conduits 423, localization sensor may be constrained (e.g., fixedly attached and/or prevented from sliding axially) at each end of flexible elongate device 400. In one example, the localization sensor is fixedly attached to distal mount 422, free-floating within sensor lumen 419, and fixedly attached at actuator 430. In some examples, a service loop can be provided within actuator 430 between a fixed localization attachment and a proximal end of flexible elongate device 400 to accommodate the varying length of sensor lumen 419 due to bending. In alternative examples, the service loop can be provided between actuator 430 and the distal end of flexible elongate device 400 or within the flexible elongate device.

In some examples, the cross-sectional shape of lumens 411-419 may change between proximal section 402 and distal section 404. For example, main lumen 411 may be keyed within proximal section 402 and unkeyed within distal section 404. As depicted in FIG. 4C, main lumen 411 of distal section 404 is unkeyed, having a circular cross-sectional shape that does not constrain the rotation of a medical instrument inserted therein. Examples of keyed lumens are discussed in greater detail below with reference to FIG. 10.

In some examples, the diameter of lumens 411-419 may change between proximal section 402 and distal section 404. Accordingly, lumens 411-419 may be tapered within transition section 406 to provide a gradual transition between the different cross-sectional shapes, e.g., a keyed lumen on the proximal side and an unkeyed lumen on the distal side.

In some examples, the flexible wall of the flexible body 410 may vary between the proximal section 402 and distal section 404. In some examples, a required bending flexibility and/or compressive strength may vary along the length of the catheter based on potential positioning within patient anatomy. Thus, the flexible wall may include a plurality of layers which can vary within a proximal section flexible wall and within a distal section flexible wall.

Despite the advantages of the above-described construction of the flexible elongate device 400 being able to actuate distal section 404 of flexible elongate device 400 by, for example, operation of the control elements 421 within conduits 423, in certain situations, once the flexible elongated device 400 is positioned in a desired pose, attempting to hold the shape of the flexible body in a desired configuration can be difficult. In addition, instances occur in which it would be advantageous to adapt the shape of the flexible body 410 based on known information about the surrounding anatomy and/or the instruments to be inserted through the main lumen 411, or other lumens. To this end, a range of stiffening mechanisms or systems are described that assist or enable holding a pose or shape of the flexible body 410. These stiffening mechanisms may be part of the steering mechanism, may be separately actuated and/or may themselves also enable steering of the flexible elongate device 400. Further, the stiffening mechanisms may use information from sensor systems, such as shape sensor 426 in the form of an optical fiber, a plurality of EM sensors distributed along the length of a flexible device, a plurality of force sensors distributed along the length of a flexible device, and/or navigation systems, such as sensor system 108 that computes the approximate location of medical instruments (such as the flexible body 410) within the anatomy of the patient and/or medical tools that are delivered through main lumen 411, to inform the control system 112 which then controls formation and holding of a shape of the flexible body 410.

In some embodiments, stiffening mechanisms, especially stiffening mechanisms with sub-elements, exhibit behaviors that can be used to stiffen the shape of the flexible body 410. In one embodiment, as shown in FIGS. 6A-6D, for example, a stiffening system or mechanism 500 uses the characteristics of the coil pipe 423 within the control element lumen 412 to stiffen the pose of the flexible body 410.

Figure 5:
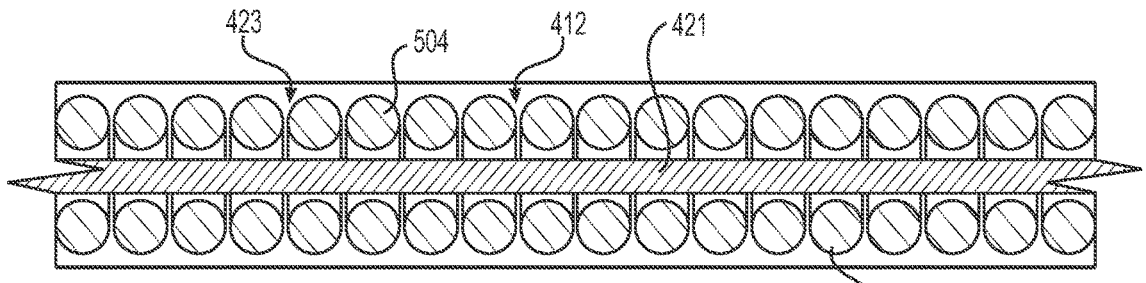
FIG. 5 is a simplified cross-sectional view of a control element conduit according to some embodiments.

FIG. 5 is an enlarged schematic showing an example of the conduit or coil pipe 423 within control element lumen 412 extending around the control element 421, such as a pull wire. Notably, in this example, the coil pipe 423 includes a plurality of windings 504. In this configuration, the windings 504 of the coil pipe 423 extend linearly in a stacked array with very little (or no) distance between them. The windings 504 are shown as rings but the coil pipe 423 can be a helical structure that extends helically along a central axis of the control element lumen 412. The control element lumen 412 and the control element 421 are shown in a straight, or un-bent, configuration.

The stiffening mechanism 500 shown in FIGS. 6A-6D, includes a restricting balloon 502 sleeved over the coil pipe 423. During actuation and steering of the flexible elongate device 400, the restricting balloon is in a passive or natural state. Once the flexible elongate device has been positioned at a desired target location, vacuum can be applied using a pump (not shown), deflating balloon 502 to interdigitate within the spaces between a plurality of windings 504 of the coil pipe. This interdigitation stiffens to hold the shape of the coil pipe 423 subsequently holding the shape and pose of the flexible elongate body 400 and providing a more stable platform for delivery of instruments through the flexible body 410.

Figures 6A, 6B:
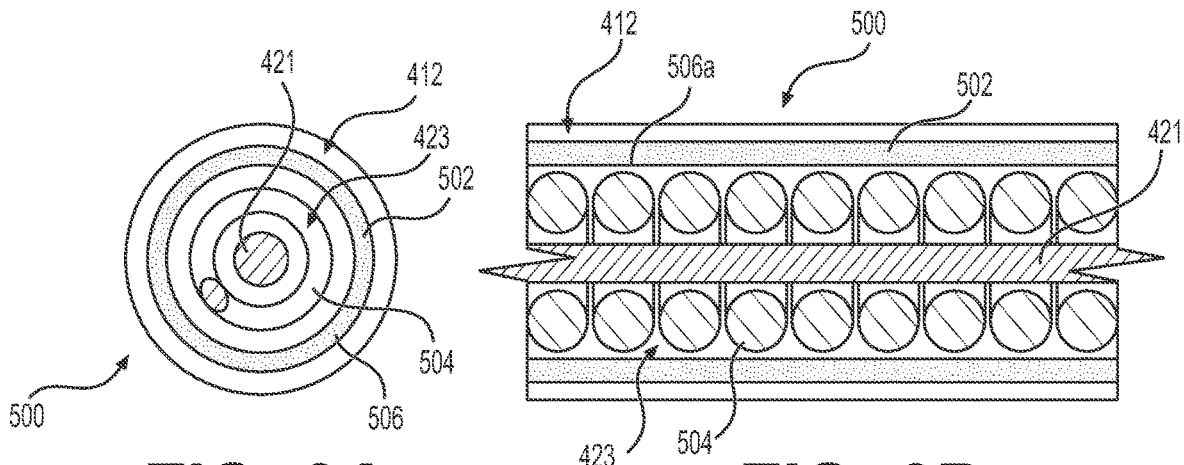
FIGS. 6A-6D are simplified diagrams of a stiffening mechanism or system according to some embodiments.

FIG. 6A shows a cross-sectional view of the control element lumen 412, and the stiffening mechanism 500 including the balloon 502. The external circle denotes the outline of the control element lumen 412 within which is a balloon layer or internal wall 506a. The balloon wall extends around (e.g., is sleeved over) the coil pipe 423. In the illustrated embodiment of FIGS. 6A-6D, the balloon 502 can be formed as a tubular structure with an open center lumen such that the balloon 502 can extend between the coil pipe 423 and an inner surface of the control element lumen 412. FIG. 6B shows a cross-sectional view taken along the longitudinal axis of a portion of the flexible body 410.

Figures 6C, 6D:
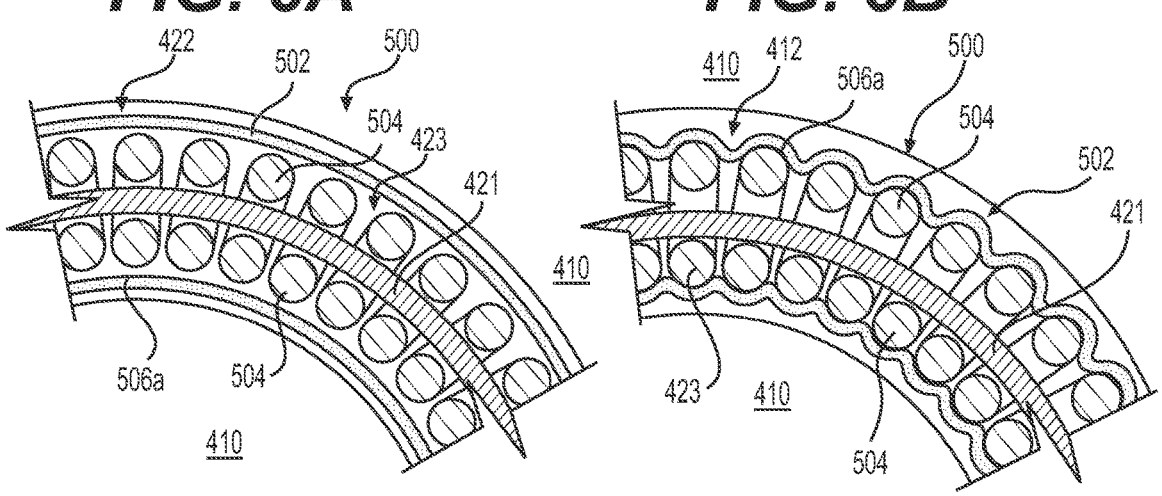

FIG. 6C shows a cross-sectional view of the control element lumen 412 bending under tension from the control element 421 (or other forces and manners of application thereof) into a curved pose along with the surrounding wall structure of the flexible body 410. In this bent pose, the windings 504 of the coil pipe 423 spread apart on the outer curvature due to tracing a longer path and compress more together on the inner curvature as they are tracing a shorter path. The balloon 502, not yet under an inflation pressure or deflation vacuum pressure, passively bends along with the control element lumen 412 and the coil pipe 423.

In FIG. 6D, the stiffening mechanism is activated by using the pump to apply a suction pressure or vacuum within the lumen of the balloon 502. The suction pressure draws the compliant balloon wall 506a inward into conforming contact with the windings 504 of the coil pipe 423. Generally, on an outside curvature where the windings are spread apart, the balloon wall 506a fills the gap between adjacent pairs of the windings. Even on an inner curvature formed in the coil pipe 423, the balloon wall 506a could achieve some interdigitation between the windings 504. In this embodiment, the adherence of the balloon wall 506a tightens the relationship between it and the windings 504 causing friction which interferes with the coil pipe 423 thus holding it in its current configuration or pose. The presence of the balloon wall 506a in between the windings 504 may wedge the adjacent pairs of windings 504 into the spread apart relationship.

FIGS. 7A-7D show another embodiment using a balloon 502 that is similar to the embodiment of FIGS. 6A-6D, except the balloon 502 is positioned within the coil pipe 423 such that an external balloon wall 506b is positioned along an inner surface of the coil pipe 423. In the illustrated embodiment of FIGS. 7A-7D, the balloon 502 can be formed as a tubular structure with an open center lumen such that the balloon 502 can extend between the control element 421 and the coil pipe 423, as shown in FIG. 7A. In an alternative embodiment, a pull wire is not used to control actuation of the elongate flexible device 400, so the balloon 502 can be positioned within a lumen of the coil pipe 423, filling the entire coil pipe lumen when inflated. In either configuration, the balloon is inflated (FIG. 7C to FIG. 7D) to adhere against and interdigitate between the windings 504 of the coil pipe 423. This embodiment could be combined with, or substituted for, the embodiment of FIGS. 6A-6D (or used with other embodiments within the scope of this disclosure) depending on the desired level of friction or mechanical blocking and strength of the hold.

Figure 10A:
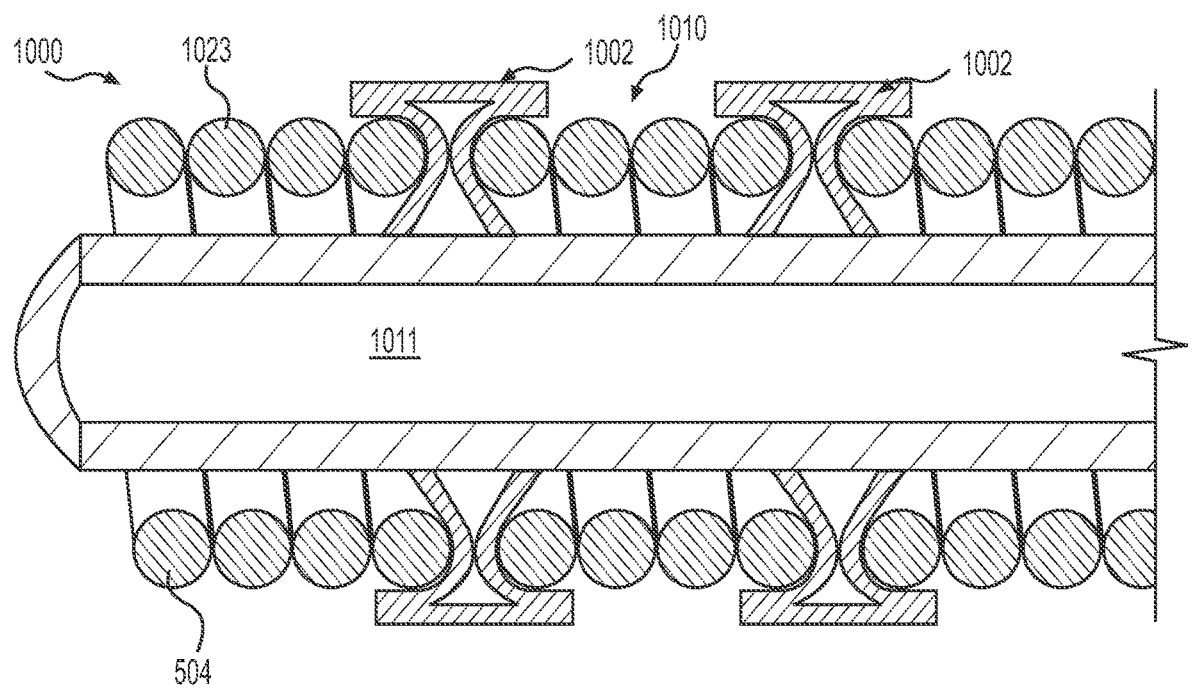
FIGS. 10A-10B are simplified diagrams of a stiffening mechanism or system according to some embodiments.

While a single coil pipe 423 is shown for FIGS. 6A-6D and 7A-7D, it should be understood that multiple coil pipes may be distributed within a single elongated flexible device 400. For example, as shown in the embodiments above of FIGS. 4A-4C, there are four control element lumens 412 and each of these could include one or more balloons 502 extending over the coil pipes 23 within the lumens 412. Alternatively or additionally, in another example without pull wires, as shown in FIG. 10A, a single coil pipe 1023 could surround a lumen 1011 of an elongated flexible device 1000 including flexible body 1010. Regardless, multiple coil pipes 423 with multiple balloons 502 or balloon portions could be used for one, several, or all the control elements 421 used in the flexible elongate device 400. Each of these balloons 502 could be selectively drawn inward with a vacuum to engage the respective windings 504 of the coils or expanded outward with pressure to engage respective windings 504 of the coils, depending on the shape or pose of the flexible body 410. Additionally, separate balloons or balloon portions could be distributed down the length of each coil pipe, such that stiffening or holding of coil pipe positions could vary down the length of the coil pipe. Thus, by controlling the amount and distribution of the applied vacuum and pressure to different balloons or balloon portions, an entire length of a flexible body can be actively controlled depending upon where and how stiff and what shape is required by the particular anatomy or particular medical procedure.

Figure 10B:
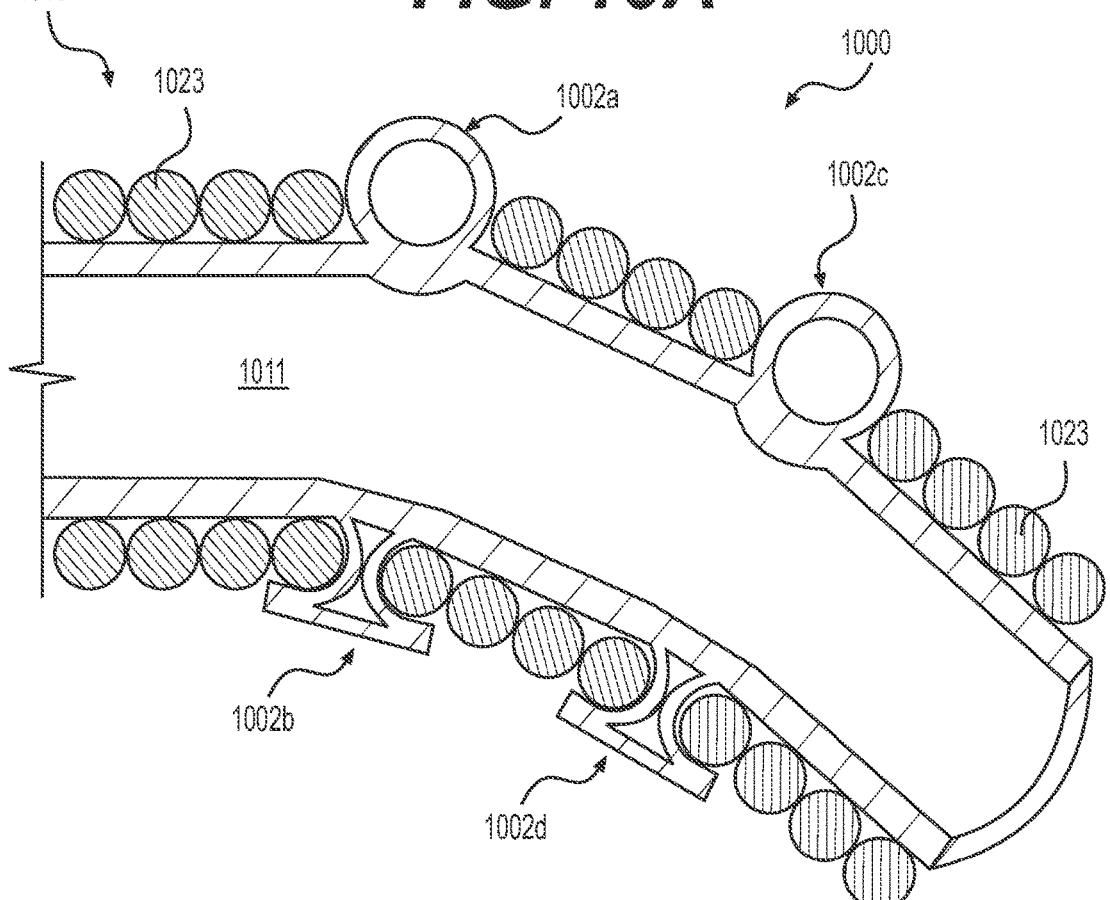

As noted above, the axial support structure 424 of the flexible body 410 may include a single large coil that encloses the main lumen 411. The structure of this larger coil, like the coil pipe 423, can be used to stiffen the flexible body 410 in a pose or shape in other embodiments. FIGS. 10A-10B show a cross-section of an embodiment including a coil pipe 1023 surrounding a lumen 1011 of an elongated flexible device 1000 including flexible body 1010. In one embodiment, a single balloon 1002 can spiral along between windings of the coil pipe 1023. As shown in FIG. 10A, the balloon is in a deflated configuration showing a cross-section which bows inward. In this embodiment, the balloon can be inflated (not shown) to force the windings of the coil pipe 1023 to expand against adjacent windings, causing the flexible body 1010 to stiffen or hold a current pose. In an alternative embodiment, a set of separate balloons or a single balloon may be partitioned into balloon portions 1002a-1002d, each positioned within different windings of the coil pipe 1023. As illustrated in FIG. 10B, each balloon portion 1002a-1002d are selectively inflated or deflated to stiffen the flexible body 1010 in a bent configuration. In this example, selected inflation of balloon portions 1002a and 1002c, can cause hold an angle between adjacent segments of the coil support structure 1023 and, along with it, the shape of the flexible body 410. On an inner bend of the flexible body 1010, balloon portions 1002b and 1002d, are deflated to allow for compression of adjacent segments along the inner bend.

The actuator 430 may include actuation for both control of the pump for inflating or drawing vacuum in the balloons and mechanisms for varying the amount of tension in the control elements 421. Thus, the actuator 430 may vary inflation and or vacuum in the balloons and tension of the control elements 421 in a coordinated relationship to achieve the desired amount of stiffness of the shape or pose of the flexible body 410. The control system 112's actuation of the balloons 502 (or other stiffening elements) and control elements 421 can be based on feedback from various sensors (such as localization sensor 426) to accomplish other objectives, such as adapting to instruments or avoiding injury to sensitive anatomy or withstanding different loading profiles. In this case, the shaping function of the control elements 421 can be facilitated by the stiffening mechanism 500, rather than the stiffening mechanism just being used to stiffen and hold a current pose or shape of the flexible body 410.

The balloon 502 can be generally constructed of similar materials as balloons for other medical applications, such as for deployment of various medical devices, such as cardiovascular devices. Such balloons can have varied beginning and end shapes depending upon the processes and molds employed in their creation. For example, balloons with large inflated diameters can be compressed down to compact configurations due to careful folding or forming. Generally, however, the balloons used in the embodiments of FIGS. 6A-6D and 7A-7D benefit from sufficient toughness to withstand multiple uses and the friction of interaction with the support structure—such as being able to be trapped or pinched between the windings 504 of the coil pipe 423. At the same time, the balloons benefit from sufficient flexibility to conform to the coil pipe 423 where spread apart to achieve a sufficient amount of friction or blocking for higher stiffnesses of holding the pose under a range of loading conditions.

The stiffening mechanism 500 could also employ other stiffening elements for holding the shape of the flexible body 410. For example, a foam could be expanded between the coil pipe 423 and the control element lumen 412 or MEMS technology employed to drive wedges or blockers between the spread apart windings 504. The balloons 502 could also be deployed in arrays of multiple balloons and the balloons themselves could be shaped to have features—such as wedge shapes configured for urging between the spread apart coils if inflated or vacuumed into contact with the coil pipe 423. Although the illustrated use of a coil pipe 423 works particularly well because of the nature of the windings 504 forming stacked, adjacent elements that spread apart during bending. Balloons could also be employed with other support structures than the coil pipe. For example, an interconnected linkage may be used in association with (or as) the control elements 421 wherein the linkages have a shape or articulation relative to each other that is stiffened upon being adhered to or wedged between by a balloon. The spacing and shape of the sub-elements could also be configured to work well with the shape and features of the stiffening elements of the stiffening mechanism. For example, wedge-shaped spaces between sub-elements of the support structure could be locked by insertion of conforming wedge-shaped stiffening elements.

It should be noted that some embodiments of the invention work well with any type of flexible elongate device 400 with the flexible body 410, wherein the flexible body has some changing structural characteristic that can be trapped, blocked, adhered to or otherwise intervened in with the operative elements of the stiffening mechanism 500 to stiffen the pose or shape of the flexible body. In previously described embodiments, the structural characteristics are within coil pipes. However, in alternative or additional examples, a support structure such as axial support structure 424 may be used in conjunction with one or more balloons surrounding the support structure or positioned within a lumen of the support structure. Particularly useful is a support structure that uses a plurality of sub-elements arranged in series, where the sub-elements exhibit differential characteristics (such as spreading apart) when adjusted into various shapes by flexing or shaping of the flexible body 410 in which they are embedded.

FIGS. 8A-8E show another embodiment of a stiffening mechanism 800 for a flexible elongate device with a flexible body 801 defining a lumen 811 and divided into a plurality of portions or segments 812. In this embodiment, the stiffening mechanism includes a plurality of nitinol wires 810 distributed circumferentially around each of the plurality of segments 812. Generally, selective activation or energizing of the nitinol wires 810 causes them to engage—by changing their length—the portion of the flexible body to hold or change its pose. The controller of the stiffening mechanism 800 can then modulate its energizing of the nitinol wires 810 based on feedback from various sensors, such as the sensor 826, to hold the pose in varying conditions. In another aspect, the nitinol wires 810 could be employed to just hold the pose of the portion of the flexible body 801 rather than be involved in shaping or steering the flexible body 410.

Figure 8A:
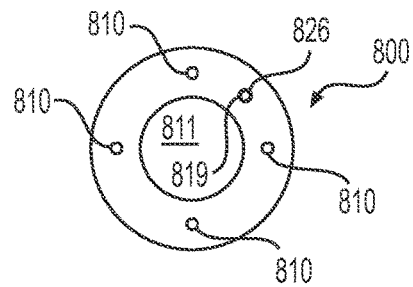
FIGS. 8A-8E are simplified diagrams of a stiffening mechanism or system according to some embodiments.
Figure 8B:
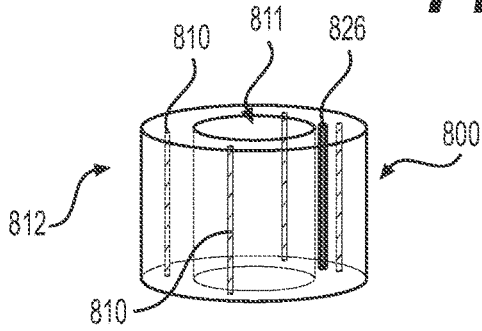
Figure 8C:
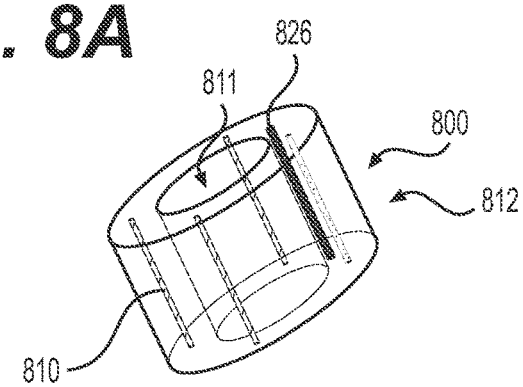

FIG. 8A shows the nitinol wires 810, in one aspect, can be embedded in a wall structure of the flexible body 801. For example, four of the nitinol wires 810 are distributed circumferentially with about 90 degrees between them. Also, FIG. 8A shows a sensor lumen such as sensor lumen 819, defined within the wall structure of the flexible body 801 about equidistant between two of the nitinol wires 810. This distribution of the nitinol wires 810 and positioning of the sensor lumen 819, with the sensors 826, such as a fiber-based shape sensor, extending therein, facilitates 360-degree bending control of the flexible body 801 by selectively controlling the amount of energization of the four nitinol wires 810 based on feedback from the shape sensor. The sensors 826 within the sensor lumen 819 may include one or more additional sensors instead of or in addition to the optical fiber shape sensor. For example, the sensors 826 may include a plurality of EM sensors distributed along the length of the flexible body 801, a plurality of force sensors distributed along the length of the flexible body 801, and/or navigation systems, such as sensor system 108 that computes the approximate location of medical instruments (such as the flexible body 801) within the anatomy of the patient and/or medical tools that are delivered through main lumen 811, to inform the control system 112 which then controls formation and holding of a shape of the flexible body 801. Fewer or more embedded nitinol wires 810 are possible with different relative distributions within the wall structure depending on the desired amount and distribution of actuation and holding forces from the stiffening mechanism 800.

Figure 8D:
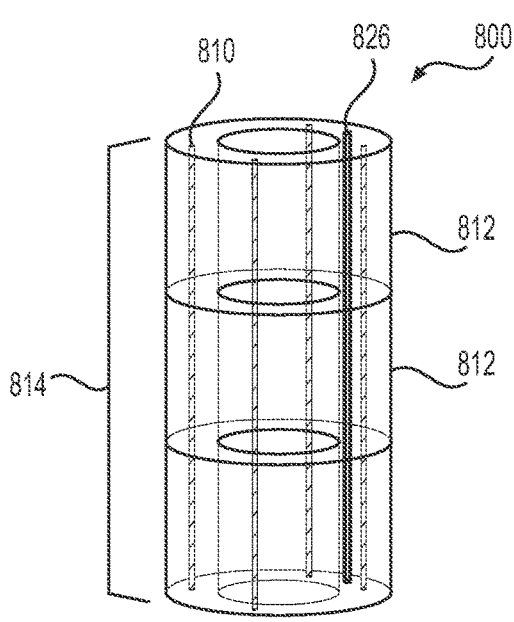
Figure 8E:
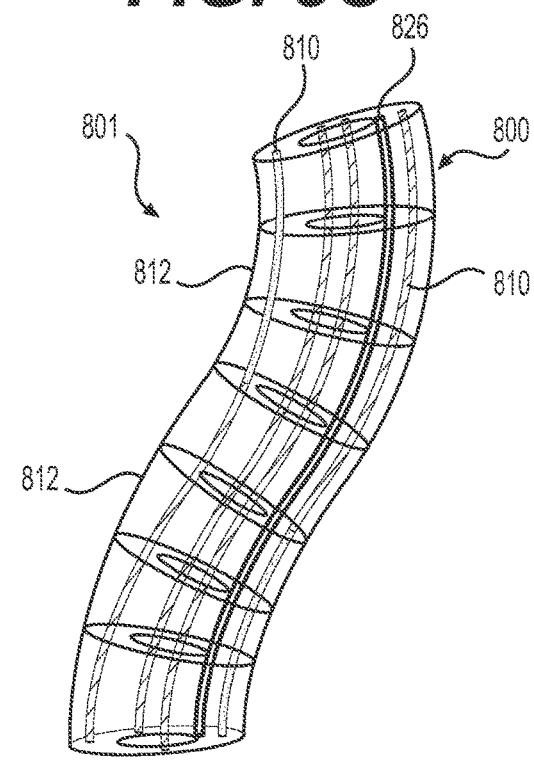

FIGS. 8B-8E show how the flexible body 801 can be formed of a plurality of portions or segments 812. Each of the segments is a short cylindrical portion of the whole flexible body 801. In this embodiment, the nitinol wires 810 are short lengths beginning and ending in the segment. The actuator 430 may be coupled to each of these lengths of nitinol wires 810 and able to energize those wires to be able to hold or adjust the pose of the segment. FIGS. 8D and 8E show how the segments 812 can be arranged end-to-end to form a longitudinal array 814 and a larger portion (or the entire) flexible body 801. In addition, FIG. 8E shows how the cumulative change in pose of each of the segments 812 results in a change in, and/or holding of shape of, the flexible body 801.

The nitinol wires are comprised of a shape memory material in the form of a nickel-titanium alloy with a transition temperature. The actuator 430 can selectively change the length of the nitinol wires by heating them, such as with electrical power, through the transition temperature to change between shapes. For example, the memorized shape of the nitinol wires may be a shorter length than the starting length. Thus, heating the nitinol wire causes it to shorten and then change the pose of the segment by compressing the segment 812. Memorized shapes could also be various curves or other configurations to help with shaping. Notably, embodiments of the present invention may also include shape memory materials other than nitinol or mechanical devices that are able to expand, retract and/or change shape to cause and hold pose changes.

In the previously described balloon and nitinol wire embodiments, the flexible body can be driven to a target location with balloon portions or nitinol wires deactivated or otherwise in a natural configuration, using pull wires or other control elements 421 for steering. Once in position, the current shape of the flexible body 410 or 801 can be measured using a shape sensing system such as tracking system 230. Then, the balloon portions 508 or nitinol wires 810 can be selectively inflated, deflated, or actuated in varying amounts to help maintain the measured shape.

In the case of nitinol wires, using the data from the optical fiber or other shape sensor, the controller system 112 can be configured to energize the appropriate nitinol wires 810 of the longer composite tube (with multiple segments) to hold its shape. Also, using shape data from the optical fiber sensor, such as sensing deviations from a desired pose or shape, forces could be applied in appropriate regions to maintain a measured shape. Additionally, the nitinol wires 810 can be used to apply greater force to increase bending moments when a stiff instrument is inserted through the device.

In another example, the balloon portions 508 can be inflated/deflated or nitinol wires can be activated, and pull wires can be additionally controllably altered in tension to maintain the measured shape. Both examples include automatic maintenance of a measured shape or the automatic hold of a pose using pull wires to further stiffen the flexible body 410.

In other embodiments, the flexible body 410/801 can be navigated within tortuous anatomy 516 in a flexible state, parked within anatomy to position a distal end of the flexible body 410/801 at a target location, then select portions of the flexible body may be stiffened or rigidized depending on different conditions. For example, during a pre-procedure planning stage, a user can identify target areas of the anatomy on a pre-operative model or map, about which one or more proximate portions of the flexible body 410/801 may be selectively rigidize. For example, target areas of the anatomy may include anatomy which are particularly sensitive (e.g., a lung airway is near the pleura, or in a different application, the path of a flexible body 410/801 is near an organ). Alternatively or additionally, imaging techniques can be used to automatically identify target areas of the anatomy. Using registration of a flexible elongate device 400 and real time tracking previously described in reference to FIGS. 2A and 2B, and by identifying the target areas of the anatomy, the flexible body 410/801 can be parked at a target, then portions of the flexible body 410/801 which are proximate the target areas of the anatomy (e.g. various discrete portions along the length of flexible body 410/801) can be selectively discretely rigidized, using stiffening mechanisms such as stiffening mechanism 500/800, to provide protection for the target area of the anatomy (e.g., sensitive anatomy) during delivery of devices through the catheter.

Figure 9A:
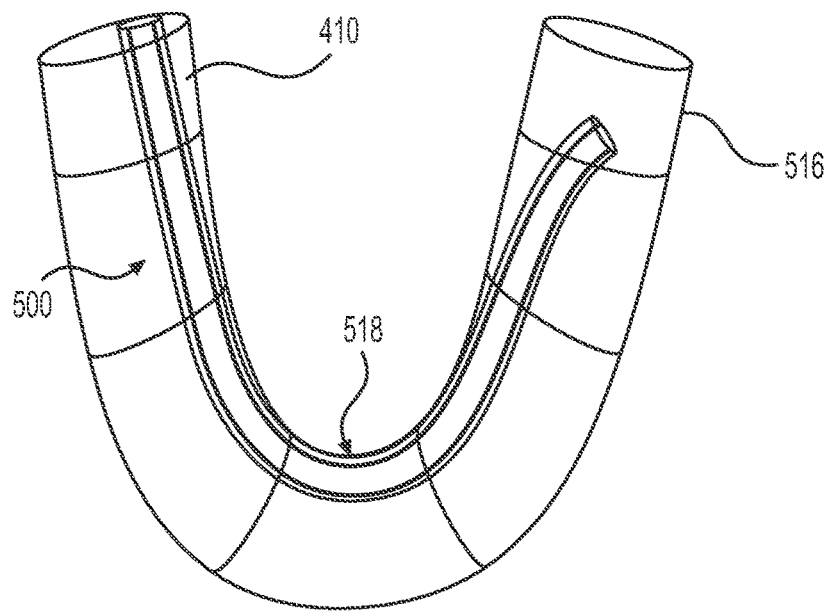
FIGS. 9A-9B are simplified diagrams of methods of using a flexible elongate device with a stiffening mechanism of other embodiments.
Figure 9B:
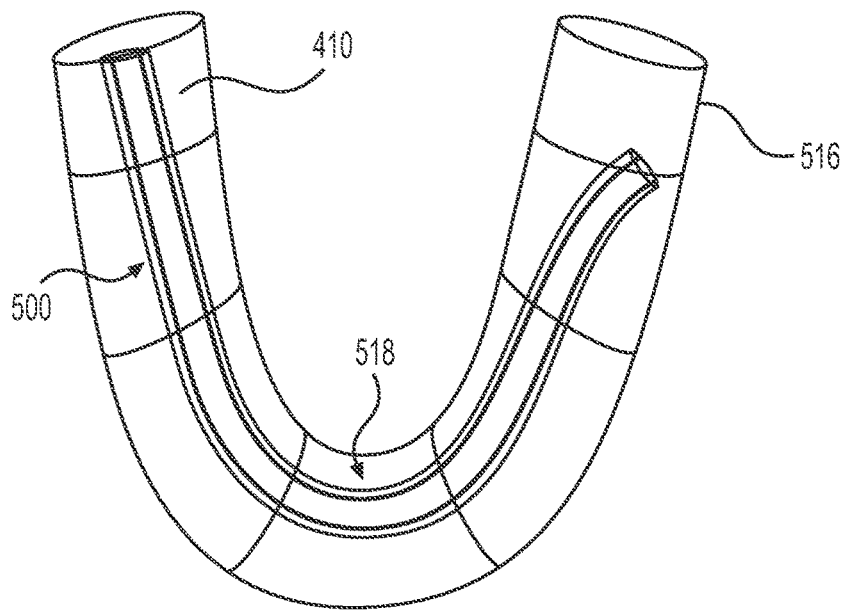

In another embodiment, the flexible body 410/801 is positioned in tortuous anatomy 516 forcing it adapt to and form tight bends, as shown in FIG. 9A. Thus, delivering a stiff device through a working lumen of the flexible body is challenging. Using selective stiffening control of the embodiments above, a tight bend 518 could be identified as a target area of the anatomy manually by a user, automatically by the control system analyzing the pre-operative model using imaging techniques, and/or by the control system 112 using shape sensing data and a threshold setting for a minimum bend radius. Along the length of the catheter positioned around the tight bend 518, the control system 112 can command the actuator 430 and stiffening mechanism 500/800 to reconfigure the shape of the flexible body 410 into a larger radius to allow for delivery of the stiff device, as shown in FIG. 9B.

More generally, in some embodiments, the control system 112 measures a current configuration of the flexible body 410/801 and determines a desired configuration of the flexible body 410/801. The current configuration of the flexible body 410/801 may include a current pose, for example, measuring the current configuration includes measuring a shape of the current pose, such as a radius of a curve along the flexible body 410/801. As discussed above, the current pose may be determined using shape sensing data from an optical fiber sensor or other shape sensor (e.g. a plurality of EM or strain sensors) along the length of the flexible body 410/801. Alternatively, shape may be determined using kinematic data describing the flexible body 410/801 and actuator 430 such as which actuators are activated, a tension in actuators, or pressure applied by actuators.

The control system 112 may determine deviations from the current configuration to a desired configuration of the flexible body 410/801. Responsive to the determined deviations, the control system 112 can command the actuator 430 to selectively stiffen one or more stiffening mechanisms 500/800 along the length of the flexible body 410/801 to apply forces in appropriate regions to position the flexible body from the current configuration to the desired configuration. For example, the stiffening mechanisms may include a plurality of the balloon portions 508/1002 and/or nitinol wires 810 distributed down the length of the flexible body 410/801 to stiffen discrete portions of the flexible body 410/801 down the length of the flexible body 410/801. Each of the stiffening mechanisms (e.g. each of the balloon portions 508/1002 and/or each of the nitinol wires 810) may be independently activated by the actuator 430.

Following the examples above, the control system 112 may determine deviations from the measured radius of a curve at a location along the flexible body 410/801 (e.g., current configuration) and the minimum bend radius (e.g., desired configuration). The minimum bend radius may be determined by the control system 112 based on receiving information describing stiffness of an instrument to be delivered by the flexible body 410/801. Accordingly, the control system 112 can command the actuator 430 to selectively stiffen ones of the stiffening mechanisms along the length of the flexible body 410/801 to apply forces in appropriate regions to position the flexible body to increase a bend radius of the curve at the location along the flexible body 410/801.

Figure 11:
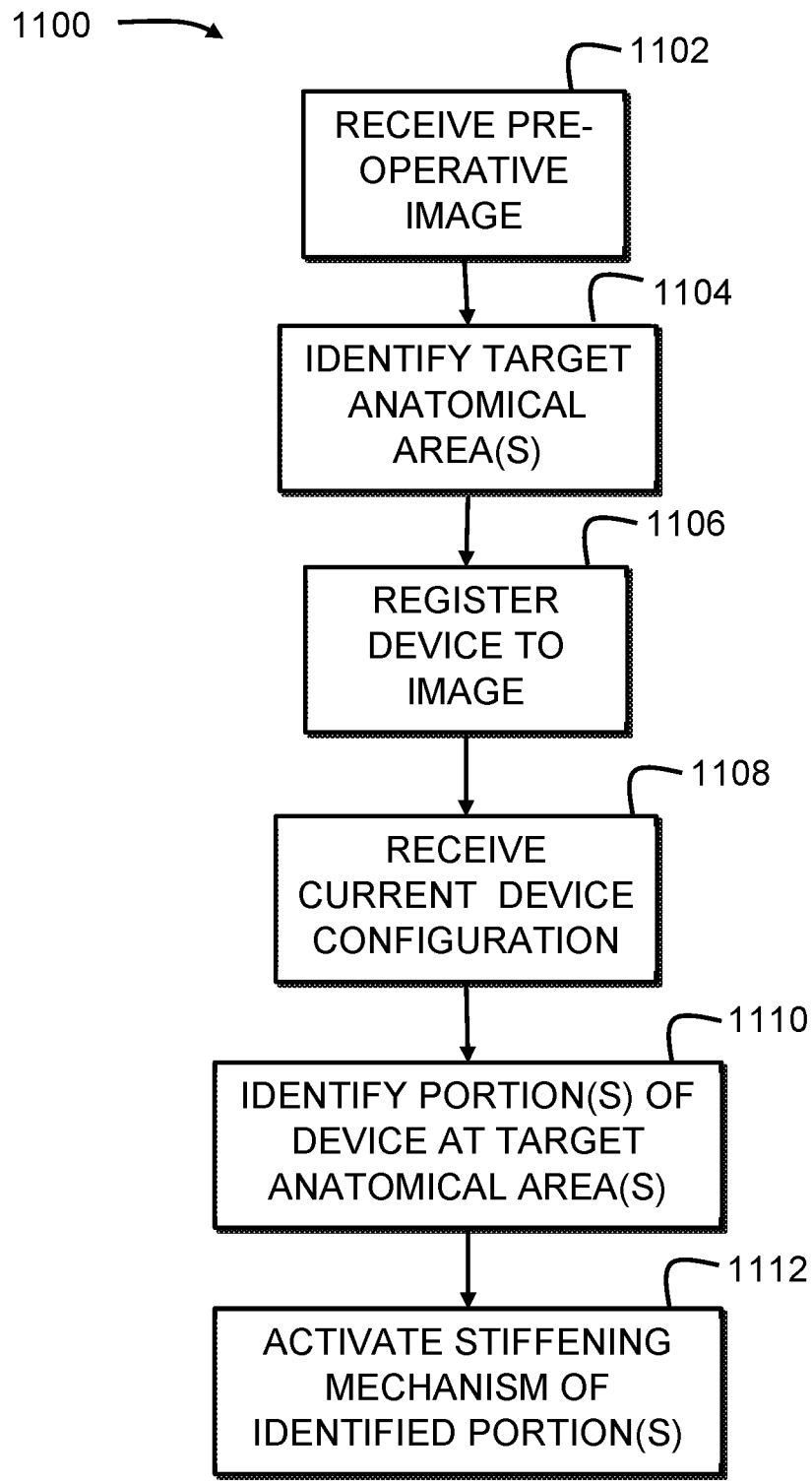
FIG. 11 is a simplified flow diagram of a method for identifying target areas of anatomy and activating a stiffening mechanism according to some embodiments.

Again following the examples above, the control system 112 may determine the desired configuration by identifying target areas of the anatomy. FIG. 11 is a simplified flow diagram of a method 1100 performed by the control system 112 for identifying target areas of the anatomy and activating a stiffening mechanism according to some embodiments. For example, the target areas of the anatomy may be identified based on the control system 112 receiving live images or preoperatively recorded surgical images and identifying portions of the flexible body 410/801 that are proximate to the target areas of the anatomy. For example, at 1102, live images or pre-operative images are received by the control system 112. The images may be received from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. In one embodiment, a pre-operative model may be generated from pre-operative images.

At 1104, target areas of the anatomy may be identified within the pre-operative model, by a user, or automatically using imaging techniques. In another embodiment, target areas of the anatomy can be identified (by users or automatically using imaging techniques) within captured live images. The identified target areas of the anatomy include sensitive anatomy or anatomy with tight bends within anatomical passageways (e.g. small radius bends where the radius is less than the minimum bend radius), for example.

At 1106, the control system 112 may be used to register the flexible body 410/801 to the live images or to the pre-operative model using sensor data from one or more sensors 426 (or 826) positioned along the flexible body 410/801, while the flexible body is being navigated within anatomy. The registration of the flexible body 410/801 to the pre-operative model/live image is based on the relative known positions between position/shape sensors (e.g. fiber optic shape sensors, EM sensors, etc.) and stiffening mechanism components 502/1002/810. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety. Systems for registering live imaging devices to a pre-operative image or imaging system are provided in PCT application PCT/US2017/017433, filed Feb. 2, 2017, disclosing, "Systems and Methods for Using Registered Fluoroscopic Images in Image-Guided Surgery" and PCT application PCT/US17/17391, filed Feb. 2, 2017, disclosing, "Systems and Methods of Pose Estimation and Calibration of Perspective Imaging System in Image Guided Surgery", which are each incorporated by reference herein in their entirety.

Information from tracking system 230 may be sent to a navigation system 232 where it is combined with information from visualization system 231 and/or the pre-operatively obtained models (e.g., anatomic models of the patient anatomy) to provide the physician or other operator with real-time position information. At 1108, the real-time position information, including the current configuration of the flexible body 410/801 is received by the control system 112. At 1110, based on the real time position information of the flexible body 410/801, and the identified target areas of the anatomy, the control system 112 can identify portions of the flexible body 410/801 that are positioned at the target areas of the anatomy. At 1112, the control system 112 can command actuators 430, to selectively stiffen one or more stiffening mechanisms 500/800 along the length of the flexible body 410/801 proximate the target areas of the anatomy (the determined portion/s of the flexible body 410/801) to provide protection for sensitive anatomy or to reconfigure the specific length of the flexible body to form a larger radius bend that is greater than or equal to the minimum bend radius.

In some examples, the real-time position information may be displayed on display system 110 of FIG. 1 for use in the control of medical instrument system 200. In some examples, a virtual image of the flexible body may be overlaid or integrated into the pre-operative model and the identified target areas of the, such as sensitive anatomy and/or tight bends may be displayed. The virtual image of the flexible body may be updated based on the real-time position information obtained from tracking system 230.

In another embodiment, the flexible body 410/801 is positioned in anatomy which may apply an external force against the flexible body 410/801. For example, anatomy may apply an external force as part of respiration, circulation, or excretion. Using selective discrete stiffening control of the embodiments above, upon detecting an external force at a location at a distal end or along the length of the flexible body 410/801, the control system 112 can command the actuator 430 to selectively stiffen discrete portions along the length of the flexible body 410/801 at the location of the external force.

Figure 12:
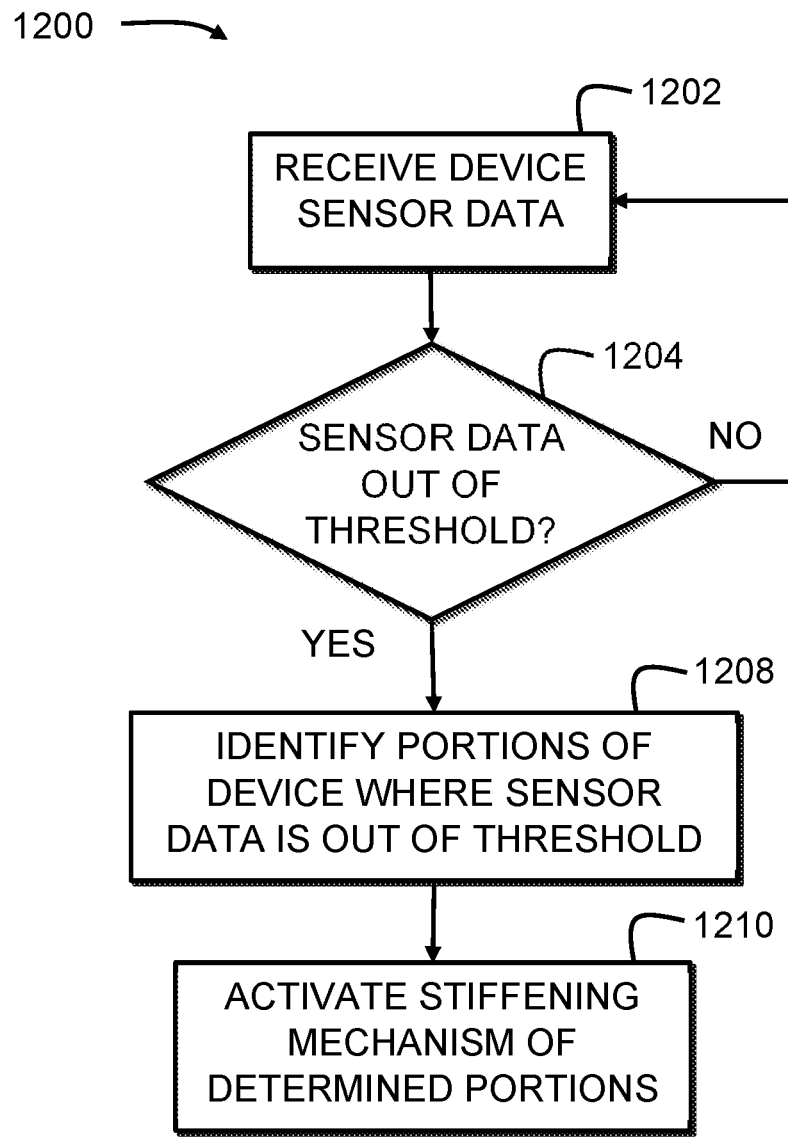
FIG. 12 is a simplified flow diagram of a method for identifying an external force and activating a stiffening mechanism according to some embodiments.

FIG. 12 is a simplified flow diagram of a method 1200 performed by the control system 112 for identifying an external force and activating a stiffening mechanism according to some embodiments. At 1202, the control system 112 receives sensor data sensor data from one or more sensors 426 (or 826) positioned along the flexible body 410/801 for detecting application of an external force. At 1204, the control system 112 determines whether any of the received sensor data is out of a predetermined threshold for identifying application of an external force to the flexible body 410/801.

For example, the external force may be detected based on detecting a change in the shape of the flexible body 410/801 as determined by the shape sensor. In some examples, the external force is detected based on a change in shape determined by the shape sensor or a change in shape viewed by live imaging that is not a result of control of the actuator 430 or movement of a medical instrument through the main lumen 411/811. In other words, the external force is detected based on a change in shape determined by the shape sensor that is independent of operation of the actuator 430 or movement of a medical instrument through the main lumen 411/811. In another example, a fiber optic shape sensor can be configured to calculate both shape and force along the length of the flexible body 410/810.

In another example, the external force may be detected based on readings from one or more force sensors positioned along the length of the flexible body 410/801. The force sensors may include one or more of a strain gauge, a load cell, a force sensing resistor, or any other suitable force sensor. Each of the force sensors may correspond to a particular location, region, or segment of the flexible body 410/801.

At 1208, the control system 112 identifies a corresponding location, region, or segment of the flexible body 410/801 where the sensor data is out of threshold. For example, the control system 112 identifies a corresponding location, region, or segment of the flexible body 410/801 where an external force is being applied to the flexible body 410/801. At 1210, upon one of the force sensors detecting where the external force is being applied to the flexible body 410/801, the control system 112 can command the actuator 430 to selectively stiffen the flexible body 410/801 at the corresponding location of the external force. In some examples, the external force detected based on the force sensors is independent of operation of the actuator 430 or movement of a medical instrument through the main lumen 411/811.

In one embodiment as described above, the flexible body 410/801 is fully positioned in anatomy such that a distal end of the flexible body 410/801 is positioned at or near an anatomical target to be used as a working channel for delivery of therapeutic and/or diagnostic tools. In order to protect anatomy, the controller may selectively stiffen discrete portions of the flexible body. Shape sensing and or external force measurements can be used to determine a portion (or plurality of portions) of the flexible body 410/801 is/are currently configured in a tight radius bend or experiencing external force. Additionally or alternatively, shape sensing can be used in conjunction with a registered pre-operative model where target areas of anatomy have been previously identified, to determine whether a portion (or plurality of portions) of the flexible body 410/801 is/are currently configured in a tight radius bend (e.g., a radius less than the minimum bend radius) or experiencing external force due to the current positioning of the flexible body 410/801 in anatomy. The controller can then selectively activate discrete stiffening elements 502/1002/810 to selectively stiffen portions of the flexible body 410/801 located at the determined portions of the flexible body 410/810.

In an alternative embodiment, the flexible body is navigated through anatomy and as a portion of the flexible body is actively inserted through a portion of anatomy that has been identified as a target area of the anatomy (e.g. tight bend, sensitive anatomy, etc.), the controller selectively activates the portion situated within the target area of anatomy. In one example, shape sensing can be used in conjunction with a registered pre-operative model by the controller to determine which portion of the flexible body is currently positioned within a target area of the anatomy. In another example, the controller can use shape sensing and/or force sensing to instantly determine which portion or plurality of portions of the flexible body is/are positioned within a tight bend or experience an excessive external force beyond a threshold. The controller can then selectively active discrete stiffening elements 502/1002/810 to selectively stiffen portions of the flexible body 410/801 located at the determined portions of the flexible body which are positioned within a target area of the anatomy, experience a tight bend, and/or experience excessive external force. The controller can propagate the selective stiffness down the length of the flexible device as the flexible device is inserted in anatomy. Accordingly, the flexible body may be stiffened in a controlled manner into a desired pose that protects anatomy from damage the flexible body as it is inserted into anatomy. For example, as a most distal section of the flexible body is positioned near to a target area of the anatomy, the controller selectively stiffens the most distal section only. Then as the flexible body is further inserted in anatomy, the most distal section is relaxed and a section just proximal the most distal section is selectively stiffened. Thus, as the flexible body is being inserted within anatomy, the flexible body can be positioned in a known and controlled pose to protect anatomy instead of allowing a fully flexible device to potentially rub or press against anatomical walls.

Embodiments above disclose embodiments of stiffening mechanism 500 that provide for selective stiffening of portions of the elongate body along its length and actuation of discrete balloon, nitinol wire or other stiffening elements for selective stiffening to hold a pose or shape. In other embodiments, selective inflation and deflation of balloon portions 1002a-1002d can be used to additionally or alternatively actuate and control steering of the elongated flexible device 1000 in addition to holding pose of the flexible body 1010 of the elongated flexible device 1000. This same ability to steer the flexible body 410 can be employed to hold the pose or shape of the flexible body 410. For example, feedback from the shape sensor 426 could be used to selectively adjust to pressure in the balloons to hold the pose or shape of the flexible body 410.

ADDITIONAL EXAMPLES

1. A method of holding a pose of a flexible body using a controller, the method comprising:
   measuring a current configuration of a flexible body based at least in part on a sensor coupled to the flexible body;
   determining a desired configuration of the flexible body; and
   selectively activating a stiffening mechanism to position the flexible body from the current configuration to the desired configuration, wherein the stiffening mechanism includes a plurality of stiffening elements distributed down the length of the flexible body.
2. The method of example 1, wherein positioning the flexible body in the desired configuration includes activating each of the plurality of stiffening elements independently.
3. The method of examples 1 or 2, wherein the current configuration includes a measured shape of the flexible body.
4. The method of example 3 further comprising identifying a small radius in the measured shape, wherein selectively activating the stiffening mechanism includes activating select ones of the plurality of the stiffening elements to increase a bend radius of the flexible body at the identified small radius in the measured shape.
5. The method of example 4 further comprising receiving information describing stiffness of an instrument to be delivered by the flexible body, wherein the identifying of the small radius in the measured shape includes determining a minimum bend radius corresponding to the stiffness of the instrument.
6. The method of any of examples 1-5, wherein determining the desired configuration comprises:
   receiving information identifying a target area of anatomy; and
   setting the desired configuration to activate select ones of the plurality of the stiffening elements at the identified target area of anatomy.
7. The method of any of examples 1-5, wherein determining the desired configuration comprises:
   receiving information identifying anatomical passageways including small radius bends; and
   setting the desired configuration to activate select ones of the plurality of the stiffening elements at the small bends.
8. The method of example 6 or 7, wherein the information received is based on live imaging.
9. The method of example 6 or 7, wherein determining the desired configuration further comprises:
   receiving a preoperatively recorded surgical image;
   registering the flexible body to the preoperatively recorded surgical image using sensor data from the sensor coupled to the flexible body;
   identifying a portion of the flexible body positioned within the identified target area of anatomy or the small bends based on the registration.
10. The method of example 6 or 7, wherein the information received is based on the preoperatively recorded surgical image.
11. The method of any of examples 1-10, wherein the current configuration includes an external force applied to the flexible body.
12. The method of any of examples 1-11, wherein the plurality of the stiffening elements includes a plurality of nitinol actuators extending within a wall structure of the flexible body, and wherein the selectively activating the stiffening mechanism includes energizing at least one of the plurality of nitinol actuators.
13. The method of any of examples 1-11, wherein the plurality of the stiffening elements includes a plurality of balloons, and wherein the selectively activating the stiffening mechanisms includes inflating or deflating at least one of the plurality of balloons.

What is claimed is:
1. A medical system comprising:
   a flexible elongate device including:
      a flexible body with a proximal end, a distal end, and at least one lumen extending between the proximal and distal ends, wherein the flexible body includes a plurality of sub-portions;
      a shape sensor extending along at least a portion of the flexible body;
      a stiffening mechanism having a plurality of stiffening elements, each of the stiffening elements positioned within one of the plurality of sub-portions, wherein the sub-portions extend along the flexible body; and
      at least one pull wire extending through the flexible body, wherein manipulation of the at least one pull wire controls a pose of the flexible body; and
      a controller connected in communication with the shape sensor, the controller configured to: (i) selectively control tension applied to the at least one pull wire to control the pose of the flexible body, and (ii) activate selected ones of the plurality of stiffening elements based in part on data received from the shape sensor to adjust stiffness of the flexible body.
2. The medical system of claim 1, wherein the activation of the selected ones of the plurality of stiffening elements is further based in part on a type of instrument received within the lumen of the flexible body.
3. The medical system of claim 2, wherein the activation of the selected ones of the plurality of stiffening elements reduces a curvature of at least a portion of the flexible body to match a stiff type of instrument.

4. The medical system of claim 1, wherein the controller is further configured to activate the selected ones of the plurality of stiffening elements based in part on anatomical information.

5. The medical system of claim 4, wherein the anatomical information includes information identifying a target area of anatomy and wherein the controller is further configured to actuate the selected ones of the plurality of stiffening elements to protect the target area of anatomy.

6. The medical system of claim 4, wherein the anatomical information includes identification of a small radius bend within anatomy and wherein the controller is further configured to actuate the selected ones of the plurality of stiffening elements to reduce a curvature of the flexible body around the small radius bend.

7. The medical system of claim 1, wherein the shape sensor includes a shape sensing fiber extending along the flexible body or a plurality of EM sensors extending along the flexible body.

8. The medical system of claim 1, wherein the stiffening mechanism includes a longitudinal balloon array having a plurality of balloon portions and wherein each of the stiffening elements is one of the plurality of balloon portions.

9. The medical system of claim 8, wherein the flexible body further includes a coil with a plurality of adjacent windings and wherein each of the plurality of balloon portions are configured to make contact with different ones of the plurality of adjacent windings with the application of pressure.

10. The medical system of claim 9, wherein the controller is further configured to selectively apply the pressure to each of the balloon portions to urge apart adjacent windings to shape the flexible body.

11. The medical system of claim 1, wherein the flexible elongate device further includes at least one coil with a plurality of adjacent windings, and wherein the stiffening mechanism includes at least one balloon configured to extend along the at least one coil.

12. The medical system of claim 11, wherein the at least one pull wire extends through the at least one coil and is coupled near the distal end of the flexible body.

13. The medical system of claim 1, wherein to activate the selected ones of the plurality of stiffening elements based in part of the data received from the shape sensor, the controller is configured to:
   determine a current configuration of the flexible body based on the data received from the shape sensor;
   determine a deviation from the current configuration to a desired configuration of the flexible body; and
   activate the selected ones of the plurality of stiffening elements based on the deviation to manipulate the flexible body into the desired configuration.

14. A method of holding a pose of a flexible body using a controller, the method comprising:
   controlling the pose of the flexible body by manipulating one or more control elements that extend through the flexible body;
   measuring a current configuration of the flexible body based at least in part on sensor data from a sensor coupled to the flexible body;
   receiving information identifying a target area of anatomy; and
   selectively activating a plurality of stiffening elements positioned within one of a plurality of sub-portions of the flexible body, the plurality of sub-portions distributed along the length of the flexible body, wherein each of the plurality of stiffening elements is activated independently based on the current configuration and the information identifying the target area of anatomy to adjust stiffness of the flexible body.

15. The method of claim 14, wherein the current configuration includes a measured shape of the flexible body.

16. The method of claim 14 further comprising identifying a small radius in the measured shape, wherein selectively activating the plurality of stiffening elements includes activating select ones of the plurality of the stiffening elements to increase a bend radius of the flexible body at the identified small radius in the measured shape.

17. The method of claim 16 further comprising receiving information describing stiffness of an instrument to be delivered by the flexible body, wherein the identifying of the small radius in the measured shape includes determining a minimum bend radius corresponding to the stiffness of the instrument.

18. The method of claim 14, wherein the information identifying the target area of anatomy includes a small radius bend within anatomical passageways.

19. The method of claim 18, wherein the selectively activating the plurality of stiffening elements includes activating select ones of the plurality of the stiffening elements at the small bend.

20. The method of claim 14, wherein the information identifying the target area of anatomy includes sensitive anatomy.

21. The method of claim 14, further comprising:
   receiving a preoperatively recorded surgical image;
   registering the flexible body to the preoperatively recorded surgical image using the sensor data from the sensor coupled to the flexible body;
   identifying a portion of the flexible body positioned within the identified target area of anatomy based on the registration.

* * * * *